United States Patent [19]
Wagner et al.

[11] Patent Number: 6,053,921
[45] Date of Patent: Apr. 25, 2000

[54] SURGICAL CABLE SYSTEM AND METHOD

[75] Inventors: Erik J. Wagner; Robert J. Jones, both of Austin, Tex.

[73] Assignee: Spinal Concepts, Inc., Austin, Tex.

[21] Appl. No.: 09/085,186

[22] Filed: May 26, 1998

Related U.S. Application Data

[63] Continuation-in-part of application No. 08/919,127, Aug. 26, 1997.

[51] Int. Cl.[7] .................................................... A61B 17/56
[52] U.S. Cl. ............................... 606/74; 606/61; 606/103
[58] Field of Search ............................... 606/74, 113, 72, 606/151, 61, 103

[56] References Cited

U.S. PATENT DOCUMENTS

| | | |
|---|---|---|
| 3,080,867 | 3/1963 | Eichinger ................................. 606/74 |
| 3,644,966 | 2/1972 | Higgins . |
| 4,401,112 | 8/1983 | Rezaian . |
| 4,433,677 | 2/1984 | Ulrich et al. . |
| 4,492,226 | 1/1985 | Belykh et al. . |
| 4,501,269 | 2/1985 | Bagby . |
| 4,503,848 | 3/1985 | Caspar et al. . |
| 4,570,618 | 2/1986 | Wu . |
| 4,604,995 | 8/1986 | Stephens . |
| 4,641,636 | 2/1987 | Cotrel . |
| 4,643,178 | 2/1987 | Nastari et al. . |
| 4,743,256 | 5/1988 | Brantigan . |
| 4,763,644 | 8/1988 | Webb . |
| 4,805,602 | 2/1989 | Puno et al. . |
| 4,834,757 | 5/1989 | Brantigan . |
| 4,878,915 | 11/1989 | Brantigan . |
| 4,887,596 | 12/1989 | Sherman . |
| 4,946,458 | 8/1990 | Herma et al. . |
| 4,950,269 | 8/1990 | Gaines, Jr. . |
| 4,961,740 | 10/1990 | Ray et al. . |
| 4,966,600 | 10/1990 | Songer et al. . |
| 4,987,892 | 1/1991 | Krag et al. . |

(List continued on next page.)

FOREIGN PATENT DOCUMENTS

| | | |
|---|---|---|
| 0019062 A1 | 11/1980 | European Pat. Off. . |
| 0597258 A1 | 10/1993 | European Pat. Off. . |
| 0578320A1 | 1/1994 | European Pat. Off. . |
| 0625336 A2 | 11/1994 | European Pat. Off. . |
| 0638292 A1 | 2/1995 | European Pat. Off. . |
| 0778007A1 | 6/1997 | European Pat. Off. . |
| 2732887A1 | 10/1996 | France . |
| 2736535A1 | 1/1997 | France . |

OTHER PUBLICATIONS

Dialog Web results for search for English–language abstract for EPO patent 0019062A1, downloaded and printed Nov. 25, 1998, 1 sheet.

International Search Report for PCT/US98/14058 dated Oct. 23, 1998.

(List continued on next page.)

*Primary Examiner*—Michael Buiz
*Assistant Examiner*—Julian W. Woo
*Attorney, Agent, or Firm*—Conley, Rose & Tayon, PC

[57] ABSTRACT

A surgical cable system and method for securing surgical cable around a portion of a human element (e.g., bone) is described. The surgical cable system may include a connector and a tensioner. The connector may be adapted to hold a pin, positionable within the connector, such that the pin may secure the cable within the connector. The pin may be repositioned, after securing the cable, to allow the cable to move freely through the connector. The cable may be oriented within the connector such that the ends of the cable are perpendicular or parallel with respect to each other. The tensioner is preferably adapted to vary the tension of the cable. The cable may be passed through the connector, around a portion of a human bone, and back through the connector. The cable may be tensioned by use of the tensioner and secured into position within the connector. The connector may include a locking portion for engaging a protrusion formed on the pin. The engagement of the protrusion with the locking portion preferably inhibits rotation of the pin.

70 Claims, 12 Drawing Sheets

U.S. PATENT DOCUMENTS

| | | |
|---|---|---|
| 5,005,562 | 4/1991 | Cotrel . |
| 5,026,373 | 6/1991 | Ray et al. . |
| 5,047,029 | 9/1991 | Aebi et al. . |
| 5,055,104 | 10/1991 | Ray . |
| 5,074,864 | 12/1991 | Cozad et al. . |
| 5,102,412 | 4/1992 | Rogozinski . |
| 5,108,399 | 4/1992 | Eitenmuller et al. . |
| 5,108,446 | 4/1992 | Wagner et al. . |
| 5,116,340 | 5/1992 | Songer et al. . |
| 5,123,926 | 6/1992 | Pishardoi . |
| 5,127,912 | 7/1992 | Ray et al. . |
| 5,129,388 | 7/1992 | Vignaud et al. . |
| 5,129,904 | 7/1992 | Illi . |
| 5,147,359 | 9/1992 | Cozad et al. . |
| 5,154,718 | 10/1992 | Cozad et al. . |
| 5,171,278 | 12/1992 | Pisharodi . |
| 5,176,678 | 1/1993 | Tsuo . |
| 5,176,680 | 1/1993 | Vignaud et al. . |
| 5,181,917 | 1/1993 | Rogozinski . |
| 5,192,321 | 3/1993 | Strokon . |
| 5,192,327 | 3/1993 | Brantigan et al. . |
| 5,201,734 | 4/1993 | Cozad et al. . |
| 5,242,445 | 9/1993 | Ashman . |
| 5,242,448 | 9/1993 | Pettine et al. . |
| 5,246,442 | 9/1993 | Ashman et al. . |
| 5,261,909 | 11/1993 | Sutterlin et al. . |
| 5,263,953 | 11/1993 | Bagby . |
| 5,281,222 | 1/1994 | Allard et al. . |
| 5,282,801 | 2/1994 | Sherman . |
| 5,290,312 | 3/1994 | Kojimoto et al. . |
| 5,290,494 | 3/1994 | Coombes et al. . |
| 5,303,718 | 4/1994 | Krajicek . |
| 5,304,179 | 4/1994 | Wagner . |
| 5,306,307 | 4/1994 | Senter et al. . |
| 5,306,309 | 4/1994 | Wagner et al. . |
| 5,312,405 | 5/1994 | Korotko et al. . |
| 5,312,410 | 5/1994 | Miller et al. . |
| 5,318,566 | 6/1994 | Miller . |
| 5,336,223 | 8/1994 | Rogers . |
| 5,336,240 | 8/1994 | Metzler et al. . |
| 5,344,422 | 9/1994 | Frigg . |
| 5,348,026 | 9/1994 | Davidson . |
| 5,357,983 | 10/1994 | Mathews . |
| 5,360,429 | 11/1994 | Jeanson et al. . |
| 5,360,431 | 11/1994 | Puno et al. . |
| 5,361,766 | 11/1994 | Nichols et al. . |
| 5,364,399 | 11/1994 | Lowery et al. . |
| 5,380,325 | 1/1995 | Lahille et al. . |
| 5,383,905 | 1/1995 | Golds et al. . |
| 5,390,683 | 2/1995 | Pisharodi . |
| 5,395,374 | 3/1995 | Miller et al. . |
| 5,397,364 | 3/1995 | Kozak et al. . |
| 5,403,315 | 4/1995 | Ashman . |
| 5,405,391 | 4/1995 | Hednerson et al. . |
| 5,415,658 | 5/1995 | Kilpela et al. ............ 606/103 |
| 5,417,690 | 5/1995 | Sennett et al. . |
| 5,423,820 | 6/1995 | Miller et al. . |
| 5,423,825 | 6/1995 | Levine . |
| 5,425,772 | 6/1995 | Brantigan . |
| 5,466,237 | 11/1995 | Byrd, III et al. . |
| 5,474,555 | 12/1995 | Puno et al. . |
| 5,480,437 | 1/1996 | Draenert . |
| 5,484,437 | 1/1996 | Michelson . |
| 5,489,307 | 2/1996 | Kuslich et al. . |
| 5,489,308 | 2/1996 | Kuslich et al. . |
| 5,496,318 | 3/1996 | Howland et al. . |
| 5,505,732 | 4/1996 | Michelson . |
| 5,507,746 | 4/1996 | Lin . |
| 5,514,180 | 5/1996 | Heggeness et al. . |
| 5,520,690 | 5/1996 | Errico et al. . |
| 5,522,899 | 6/1996 | Michelson . |
| 5,527,341 | 6/1996 | Gogolewski et al. . |
| 5,531,746 | 7/1996 | Errico et al. . |
| 5,531,751 | 7/1996 | Schultheiss et al. . |
| 5,536,270 | 7/1996 | Songer et al. . |
| 5,536,271 | 7/1996 | Daly et al. . |
| 5,545,165 | 8/1996 | Biedermann et al. . |
| 5,549,608 | 8/1996 | Errico et al. . |
| 5,549,612 | 8/1996 | Yapp et al. . |
| 5,554,157 | 9/1996 | Errico et al. . |
| 5,563,124 | 10/1996 | Damien et al. . |
| 5,569,248 | 10/1996 | Mathews . |
| 5,569,253 | 10/1996 | Farris et al. . |
| 5,571,192 | 11/1996 | Schönhöffer . |
| 5,575,792 | 11/1996 | Errico et al. . |
| 5,578,033 | 11/1996 | Errico et al. . |
| 5,584,834 | 12/1996 | Errico et al. . |
| 5,586,984 | 12/1996 | Errico et al. . |
| 5,593,409 | 1/1997 | Michelson . |
| 5,601,553 | 2/1997 | Trebing et al. . |
| 5,601,556 | 2/1997 | Pishardoi . |
| 5,603,713 | 2/1997 | Aust et al. . |
| 5,607,424 | 3/1997 | Tropiano . |
| 5,607,425 | 3/1997 | Rogozinski . |
| 5,607,426 | 3/1997 | Ralph et al. . |
| 5,607,429 | 3/1997 | Hayano et al. . |
| 5,607,430 | 3/1997 | Bailey . |
| 5,609,592 | 3/1997 | Brumfield et al. . |
| 5,609,593 | 3/1997 | Errico et al. . |
| 5,609,594 | 3/1997 | Errico et al. . |
| 5,609,596 | 3/1997 | Pepper . |
| 5,609,635 | 3/1997 | Michelson . |
| 5,609,636 | 3/1997 | Kohrs et al. . |
| 5,611,800 | 3/1997 | Davis et al. . |
| 5,611,801 | 3/1997 | Songer . |
| 5,613,967 | 3/1997 | Engelhardt et al. . |
| 5,616,144 | 4/1997 | Yapp et al. . |
| 5,620,443 | 4/1997 | Gertzbein et al. . |
| 5,624,441 | 4/1997 | Sherman et al. . |
| 5,626,579 | 5/1997 | Muschler et al. . |
| 5,628,740 | 5/1997 | Mullane . |
| 5,628,756 | 5/1997 | Barker, Jr. et al. . |
| 5,630,816 | 5/1997 | Kambin . |
| 5,632,747 | 5/1997 | Scarborough et al. . |
| 5,634,925 | 6/1997 | Urbanski . |
| 5,643,260 | 7/1997 | Doherty . |
| 5,643,264 | 7/1997 | Sherman et al. . |
| 5,643,265 | 7/1997 | Errico et al. . |
| 5,645,084 | 7/1997 | McKay . |
| 5,645,544 | 7/1997 | Tai et al. . |
| 5,645,549 | 7/1997 | Boyd et al. . |
| 5,645,598 | 7/1997 | Brosnahan, III . |
| 5,647,873 | 7/1997 | Errico et al. . |
| 5,649,927 | 7/1997 | Kilpela et al. . |
| 5,651,283 | 7/1997 | Runciman et al. . |
| 5,651,789 | 7/1997 | Cotrel . |
| 5,653,708 | 8/1997 | Howland . |
| 5,653,709 | 8/1997 | Frigg . |
| 5,653,763 | 8/1997 | Errico et al. . |
| 5,658,289 | 8/1997 | Boucher et al. . |
| 5,658,337 | 8/1997 | Kohrs et al. . |
| 5,658,516 | 8/1997 | Eppley et al. . |
| 5,662,653 | 9/1997 | Songer et al. . |
| 5,665,088 | 9/1997 | Gil et al. . |
| 5,665,112 | 9/1997 | Thal . |
| 5,665,122 | 9/1997 | Kambin . |
| 5,667,506 | 9/1997 | Sutterlin . |
| 5,667,507 | 9/1997 | Corin et al. . |
| 5,667,508 | 9/1997 | Errico et al. . |
| 5,668,288 | 9/1997 | Storey et al. . |
| 5,669,909 | 9/1997 | Zdeblick et al. . |
| 5,669,910 | 9/1997 | Korhonen et al. . |

| | | |
|---|---|---|
| 5,669,911 | 9/1997 | Errico et al. . |
| 5,671,695 | 9/1997 | Schroeder . |
| 5,672,175 | 9/1997 | Martin . |
| 5,674,222 | 10/1997 | Berger et al. . |
| 5,674,295 | 10/1997 | Ray et al. . |
| 5,674,296 | 10/1997 | Bryan et al. . |
| 5,676,665 | 10/1997 | Bryan . |
| 5,676,666 | 10/1997 | Oxland et al. . |
| 5,676,701 | 10/1997 | Yuan et al. . |
| 5,676,703 | 10/1997 | Gelbard . |
| 5,681,311 | 10/1997 | Foley et al. . |
| 5,681,312 | 10/1997 | Yuan et al. . |
| 5,683,391 | 11/1997 | Boyd . |
| 5,683,392 | 11/1997 | Richelsoph et al. . |
| 5,683,393 | 11/1997 | Ralph . |
| 5,683,394 | 11/1997 | Rinner . |
| 5,688,272 | 11/1997 | Montague et al. . |
| 5,688,273 | 11/1997 | Errico et al. . |
| 5,688,274 | 11/1997 | Errico et al. . |
| 5,688,279 | 11/1997 | McNulty et al. . |
| 5,688,280 | 11/1997 | Booth, Jr. et al. . |
| 5,690,629 | 11/1997 | Asher et al. . |
| 5,690,630 | 11/1997 | Errico et al. . |
| 5,690,631 | 11/1997 | Duncan et al. . |
| 5,690,632 | 11/1997 | Schwartz et al. . |
| 5,690,633 | 11/1997 | Taylor . |
| 5,690,842 | 11/1997 | Panchison . |
| 5,693,046 | 12/1997 | Songer et al. . |
| 5,693,053 | 12/1997 | Estes . |
| 5,693,100 | 12/1997 | Pisharodi . |
| 5,697,929 | 12/1997 | Mellinger . |
| 5,697,977 | 12/1997 | Pisharodi . |
| 5,700,291 | 12/1997 | Kuslich et al. . |
| 5,700,292 | 12/1997 | Margulies . |
| 5,702,391 | 12/1997 | Lin . |
| 5,702,392 | 12/1997 | Wu et al. . |
| 5,702,393 | 12/1997 | Pfaifer . |
| 5,702,394 | 12/1997 | Henry et al. . |
| 5,702,395 | 12/1997 | Hopf . |
| 5,702,396 | 12/1997 | Hoenig et al. . |
| 5,702,399 | 12/1997 | Kilpela . |
| 5,702,449 | 12/1997 | McKay . |
| 5,702,450 | 12/1997 | Bisserie . |
| 5,702,451 | 12/1997 | Biedermann et al. . |
| 5,702,452 | 12/1997 | Argenson et al. . |
| 5,702,453 | 12/1997 | Rabbe et al. . |
| 5,702,454 | 12/1997 | Baumgartner . |
| 5,702,455 | 12/1997 | Saggar . |
| 5,704,936 | 1/1998 | Mazel . |
| 5,704,937 | 1/1998 | Martin . |
| 5,707,372 | 1/1998 | Errico et al. . |
| 5,707,395 | 1/1998 | Li . |
| 5,709,681 | 1/1998 | Pennig . |
| 5,709,682 | 1/1998 | Medoff . |
| 5,709,683 | 1/1998 | Bagby . |
| 5,709,684 | 1/1998 | Errico et al. . |
| 5,709,685 | 1/1998 | Dombrowski et al. . |
| 5,709,686 | 1/1998 | Talos et al. . |
| 5,713,841 | 2/1998 | Graham . |
| 5,713,898 | 2/1998 | Stucker et al. . |
| 5,713,899 | 2/1998 | Marnay et al. . |
| 5,713,900 | 2/1998 | Benzel et al. . |
| 5,713,903 | 2/1998 | Sander et al. . |
| 5,713,904 | 2/1998 | Errico et al. . |
| 5,716,355 | 2/1998 | Jackson et al. . |
| 5,716,356 | 2/1998 | Biederman et al. . |
| 5,716,357 | 2/1998 | Rogozinski . |
| 5,716,358 | 2/1998 | Ochoa et al. . |
| 5,716,359 | 2/1998 | Ojima et al. . |
| 5,716,415 | 2/1998 | Steffee . |
| 5,716,416 | 2/1998 | Lin . |
| 5,720,746 | 2/1998 | Soubeiran . |
| 5,720,747 | 2/1998 | Burke . |
| 5,720,748 | 2/1998 | Kuslich et al. . |
| 5,720,751 | 2/1998 | Jackson . |
| 5,722,977 | 3/1998 | Wilhelmy . |
| 5,733,284 | 3/1998 | Martin . |
| 5,782,831 | 7/1998 | Sherman et al. . |

OTHER PUBLICATIONS

Danek Group, Inc. Medical Division Publication entitled, "TSRH Spinal System—Unmatched versatility," 1992, pp. 1–4.

Danek Surgical Technique Manual entitled, "TSRH Spinal Implant System," Date 3731, pp. 1–16.

Danek Surgical Technique Manual entitled, "TSRH Crosslink," Date 3731, pp. 1–8.

Dickman Curtis A., et al, BNI Quarterly Publication entitled, "Techniques of Screw Fixation of the Cervical Spine," vol. 9. No. 4, Fall 1993, pp. 27–39.

Slone et al, RadioGraphics Publication entitled, "Spinal Fixation," vol. 13 No. 2, Mar. 1993, pp. 341–356.

Synthes Spine Publication entitled, "The Universal Spinal System—Internal Fixation for the Spine," 1994, pp. 1–15.

AcroMed Publication entitled, "The ISOLA Spinal System—Versatility, simplicity and minimal profile in the surgical treatment of the spine," 1994, pp. 1–15.

AcroMed Corporation Publication entitled, "ISOLA® Transverse Rod Connectors: Principles and Techniques," Date 3731, pp. i, ii, 1–8.

DANEK Publication entitled, "AXIS—Fixation System," 1993, pp. 1–6.

Synthes Publication entitled, "Small Notched Titanium Reconstruction Plate System," 1996, pp. 1–6.

J. Neurosurg Publication entitled, "Posterior plates in the management of cervical instability: long–term results in 44 patients," vol. 81, 1994, pp. 341–349.

BNI Quarterly Publication entitled, "Lateral Mass Posterior Plating and Facet Fusion for Cervical Spine Instability," vol. 7, No. 2, 1991, pp. i, ii, 1–12.

Beadling, Lee, Orthopedics Today Publication entitled, "FDA Clears Spinal Cages for Interbody Lumbar Fusion," pp. 1–2.

MedPro Month Publication entitled, "Trends in Spine & Disk Surgery," vol. VI, No. 11–12, pp. 280–284.

Surgical Dynamics Ray Threaded Fusion Cage Device Surgical Technique Manual, pp. 1–10.

Surgical Dynamics Ray Treaded Fusion Cage, pp. 1–6.

AcroMed Publication entitled, "AcroMed Spinal Solutions for Cervical Pathologies," 07–95, pp. 1–8.

Codman Publication entitled, "Sof'wire Cable System," 6 pages.

Huhn, Stephen L. et al, "Posterior Spinal Osteosynthesis for Cervical Fracture/Dislocation Using a Flexible Multistrand Cable System: Technical Note," Neurosurgery, vol. 29, No. 6, 1991, pp. 943–946.

Dickman, Curtis A. et al, "Wire Fixation for the Cervical Spine: Biomechanical Principles and Surgical Techniques," BNI Quarterly, vol. 9, No. 4, Fall 1993, pp. 2–16.

Publication by AcroMed entitled, "ACROMED Cable System by Songer," Sep. 1993, 4 pages.

M. Aebi, MD, et al, "Treatment of Cervical Spine Injuries with Anterior Plating: Indications, Techniques, and Results," vol. 16, No. 3S, Mar., 1991 Supplement, pp. S38–S45.

Foley, M.D. et al, "Aline Anterior Cervical Plating System," Smith & Nephew Richards, Inc. Orthopaedics Catalog Information, Sep. 1996, pp. 1–16.

Lowery, Gary L., M.D., Ph.D., Sofamor Danek Group, Inc. Publication entitled, "Orion Anterior Cervical Plate System: Surgical Technique," 1994, pp. 1–24.

Apfelbaum, R., M.D., Aesculap Scientific Information publication entitled, "Posterior Transarticular C1–2 Screw Fixation for Atlantoaxial Instability," 1993, pp. 1–15.

Danek Titanium Cable System publication by Danek Group, Inc., 1994, 6 pages.

Publication entitled, "Spinal Disorders", 4 pages.

O'Brien, John P., Ph.D., Orthopaedic Product News Article entitled, "Interbody Fusion of the Lumbar Spine," pp. 1–3.

Roy et al, "Variation of Young's Modulus and Hardness in Human Lumbar Vertebrae Measured by Nanoindentation", pp. 1–4.

Sofamor Danek publication entitled, "Atlas Cable System: Evolution of the Cable System for Spinal Applications," 1995, 2 pages.

AcroMed publication entitled, "AcroMed Songer Cable System: Ordering information for Implants and Instruments," Apr. 1996, 4 pages.

Songer, Matthew, M.D., "Acromed Cable System by Songer: Cervical Technique Manual," pp. 1–17.

Songer, Matthew N., M.D., "ACROMED Cable System by Songer: Technique Manual," 1993, pp. 1–20.

Oxland, Thomas R., Ph.D., et al, SpineTech Inc. Publication entitled, "Biomechanical Rationale—The BAK Interbody Fusion System: An Innovative Solution," pp. 1–16.

SpineTech, Inc. publication entitled, "Patient Information on Spinal Fusion Surgery and the BAK Interbody Fusion System," 10 pages.

SpineTech, Inc. publication entitled, "BAK/Cervical Interbody Fusion System," 1994, 2 pages.

SpineTech, Inc. publications entitled, "Instrumentation BAK Interbody Fusion System," "Biomechanics BAK Interbody Fusion System," and "Porosity BAK Interbody Fusion System," 1996, 12 pages.

SpineTech, Inc. publication entitled, "The BAK Interbody Fusion System," 1996, 4 pages.

Depuy Motech, Inc. publication entitled, "Moss Miami 3–Dimensional Spinal Instrumentation: Taking Spinal Instrumentation to a New Dimension," 1995, 8 pages.

Shufflebarger, Harry L., M.D., "Moss Miami Spinal Instrumentation System: Methods of Fixation of the Spondylopelvic Junction," *Lumbosacral and Spinopelvic Fixation,*1996 by Raven Publishers, Philadelphia, pp. 381–393.

Shufflebarger, Harry L., M.D., Depuy Motech publication entitled, "Clinical Issue: Rod Rotation in Scoliosis Surgery," 5 pages.

AcroMed publication entitled, "Instruments," 3 pages.

SpineTech, Inc. publication entitled, "The Bone Harvester," 1996, 2 pages.

Wright Medical Technology Publication entitled, "Versalok Low Back Fixation System," 1996, pp. 1–4.

Danek Medical, Inc. Publication entitled, "TSRH Lumbar System," 1991, pp. 1–4.

Spinal Concepts Inc. publication entitled "The BacFix ss—Posterior Lower Back Fixation System—Written Surgical Technique," 1997, pp. 1–11.

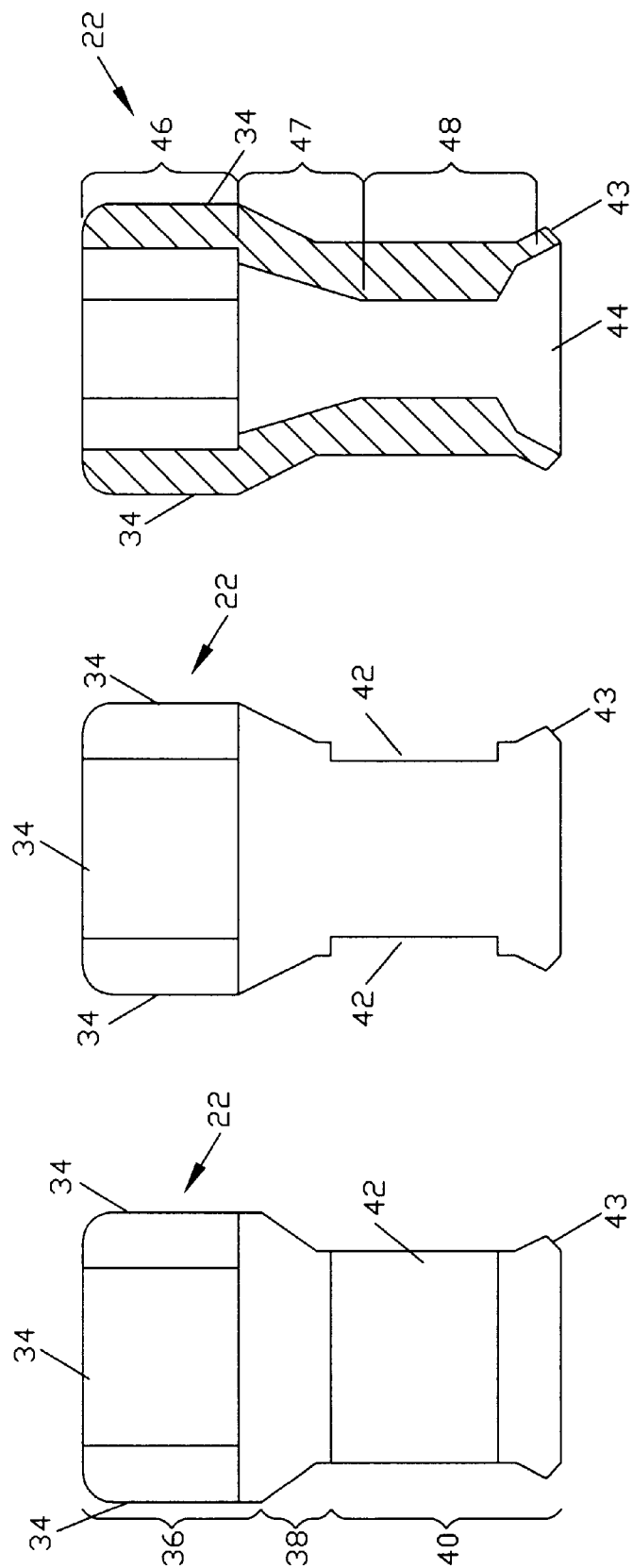

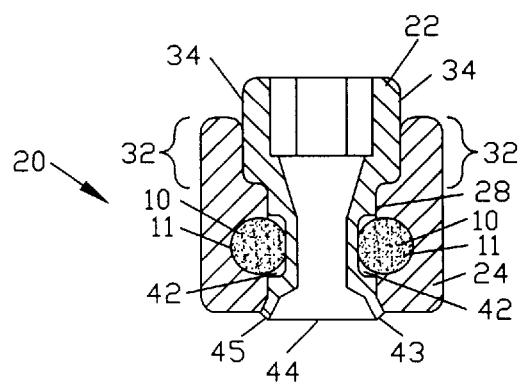
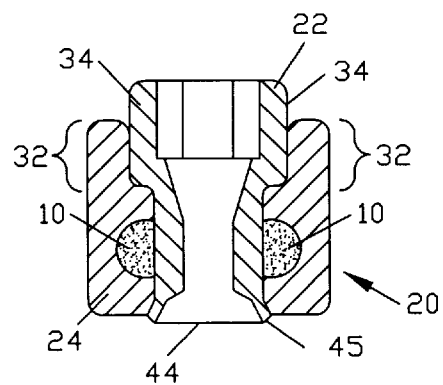
FIG. 10     FIG. 11
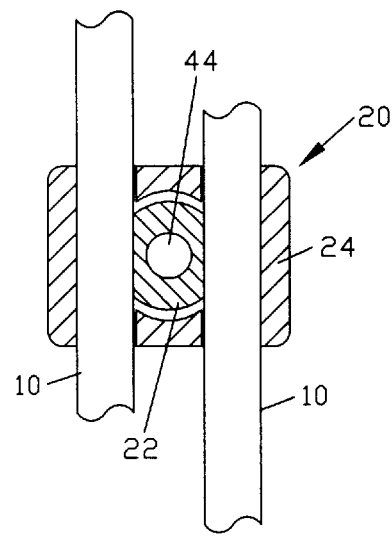
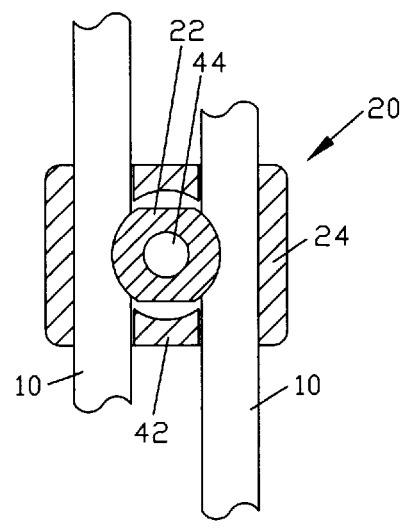
FIG. 12     FIG. 13

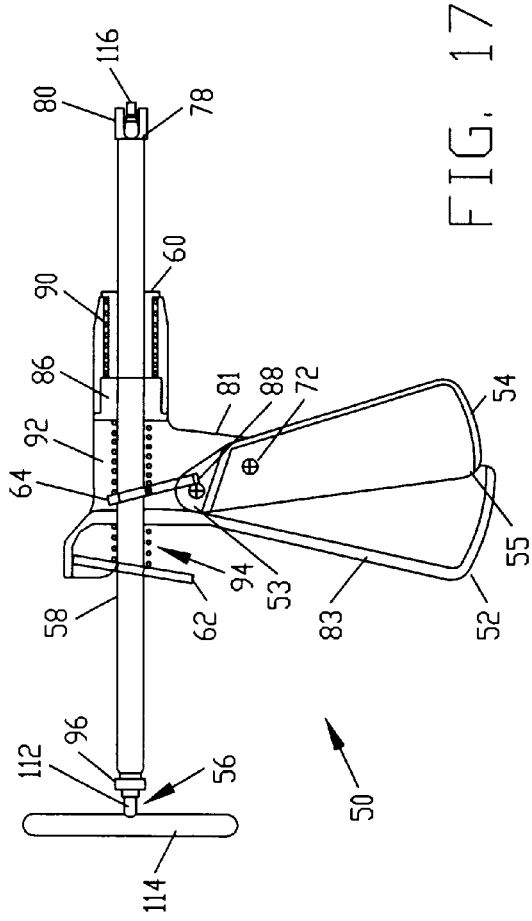
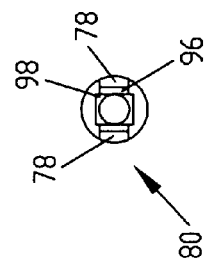
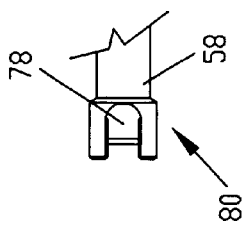

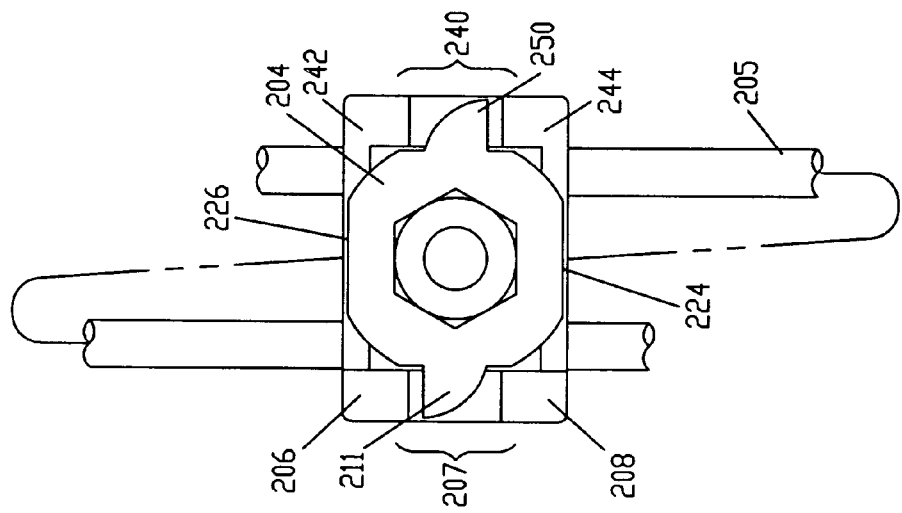
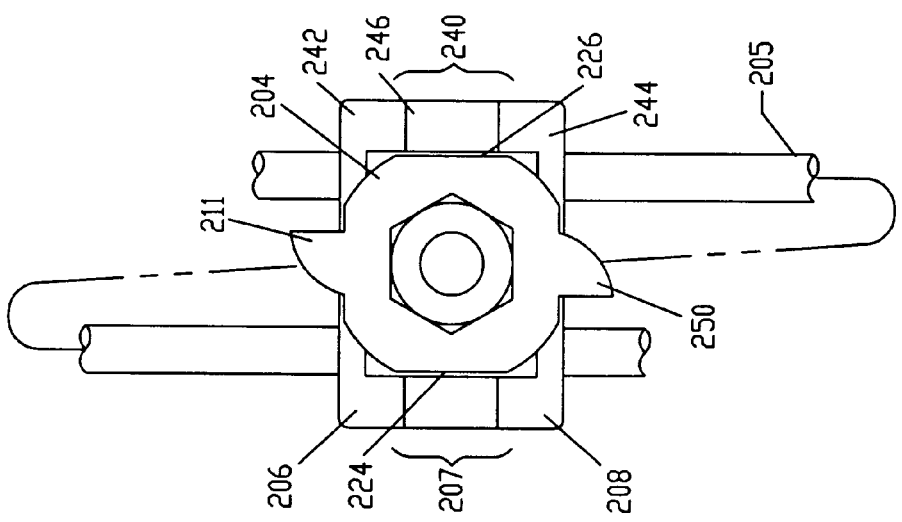

SURGICAL CABLE SYSTEM AND METHOD

PRIOR APPLICATION

This application is a continuation-in-part of U.S. patent application Ser. No. 08/919,127 filed on Aug. 26, 1997.

BACKGROUND OF THE INVENTION

1. Field of the Invention

The present invention generally relates to surgical cable systems and the like. More particularly, an embodiment of the invention relates to a method and apparatus for securing surgical cable around a portion of a human bone.

2. Description of the Related Art

Surgical cables are used in a variety of surgical procedures, some examples include: spine surgery; total hip arthroplasty; fracture fixation; closure of the sternum following open heart surgery; and oral/facial surgery to repair mandibular fractures. In these and other surgical procedures the cable may be used to set and secure bone portions in the proper orientation during the healing process.

Fractures of the vertebrae in the spinal column are very difficult to immobilize, often requiring the use of internal pins, cables and/or rods. One frequently used procedure involves wiring the fractured vertebra to one or more adjacent vertebrae to secure the vertebra in an ideal position for healing. Another method involves wiring the fractured vertebra to a rod that is similarly joined to other vertebrae. Both of these methods, as well as other techniques for spinal repair, rely on the use of cables which are secured around a portion of a vertebra.

A number of methods for encircling bone portions with surgical cables have been developed. Most of these techniques involve passing a cable around a portion of the bone and securing the cable in position using a crimp. Example of cabling apparatus and methods are illustrated in U.S. Pat. Nos. 4,966,600; 5,395,374; 5,415,658; 5,423,820; and 5,569,253. Each of these patents is incorporated by reference as if fully set forth herein.

The Acromed™ Cable System by Songer, as shown in U.S. Pat. No. 4,966,600, represents a cabling system that relies on the use of a metal crimp member to secure a cable in a loop. In one embodiment of the Acromed™ system a crimp member is affixed to one end of the cable. The cable may then be passed partially through a connector. The crimp member may inhibit the cable from passing entirely through the connector. The cable may then be looped around the bone portion and passed again through the connector. A tensioning device is used to tighten the cable around the bone portion, and another crimp member is applied to the portion of the wire extending out from the connector to fix the cable in position.

The Acromed™ system relies on crimp members to attempt to irreversibly secure the cable in position. This feature may present difficulties if a number of cables are used in series since it is often necessary to retighten some of the cables as other cables are added. To overcome this problem a double crimp technique is commonly used. In this technique the cable is passed through two crimp members before the cable is tensioned. After tensioning, the top crimp member may be affixed to the cable. When the cable becomes loosened, it may be re-tensioned and the lower crimp member affixed to the cable. The upper crimp member may be trimmed off after the second crimp member is fastened to the cable. A disadvantage of this approach is that the number of re-tensions that may be performed is determined by the number of crimp members attached to the cable before the initial tensioning. If additional re-tensioning is required after the last crimp member has been attached to the cable, the cable may need to be removed and a new cable attached.

An orthopedic cable apparatus manufactured by Danek Medical Inc., as shown in US. Pat. Nos. 5,395,374 and 5,423,820, appears to overcome these problems. The apparatus consists of three separate parts: a double-apertured L-shaped crimp; a cable clamp; and a tensioning tool. The Danek system affixes one end of the cable to the double-apertured L-shaped crimp. The cable is then looped around the bone portion and passed through the other aperture of the L-shaped crimp. The cable is then passed through a cable clamp, and further through a tensioner. The tensioning device is used to tighten the cable around the vertebra. Once the appropriate tension is achieved the cable clamp is tightened to temporarily fix the cable in position. Since the cable clamp acts as a non-permanent securing device, the user is free to re-tension the cable a number of times during use. When the user is finished, the cable is fixed into position by crimping the second crimp portion of the L-shaped crimp onto the cable. The Danek cabling system avoids the need for multiple crimps, as used by the Acromed™ system, however, it still relies on crimps to secure the cable in position.

A disadvantage to the use of crimps for securing a cable in position is that the crimps may be highly unreliable. The crimps are typically compressed by the user to affix them to the cable. However, it may be very difficult to control the percentage of deformation of the crimp such that a predictable and consistent amount of deformation may be produced. If the crimp is over deformed some of the cable strands may be sheared off, reducing the strength of the cable at the connection. Conversely, if the crimp is under deformed, the crimp may be incapable of preventing the cable from loosening after the procedure is finished.

Another problem encountered when using cable systems is that they force the cable into a specific position relative to the point where the cable crosses itself. In some cases there is an advantage for the ends of the cable to be in a parallel orientation. Such an orientation allows a minimal profile of the connector. A low profile width is generally desired to minimize sinus formation and soft tissue irritation. The parallel orientation may sometimes cause a sharp bend in the cable, thereby creating stress in the system. To overcome this stress it is desirable for the ends of the cable to be in a perpendicular orientation relative to each other.

The Acromed™ apparatus, as shown in U.S. Pat. No. 4,966,600, may be used in a number of ways in order to achieve the desired cable orientation. In one method the cable comprises a permanently looped eyelet end. The other end of the cable may be passed through the eyelet to form a loop in which the ends of the cable are oriented in a perpendicular fashion. In another method the ends of the cable may be held in a parallel orientation by using a special connector designed for this purpose. The Danek system, as shown in U.S. Pat. No. 5,569,253, is also designed for use with the ends of the cable in a parallel or perpendicular orientation. The Danek system relies on the use of specially designed connectors for each orientation. Neither the Acromed or the Danek systems describe a single connector which would allow the cable to be positioned in both a parallel and a perpendicular orientation.

The above mentioned methods and systems inadequately address, among other things, the need for an apparatus that allows re-tensioning of the cable, as well as multiple orientations of the cable. The devices also rely on crimps affixed to the cables to hold the cable in place. As mentioned before, such crimps may be unreliable. It is therefore desirable that a cable system be derived that incorporates, in a single device, the ability to allow the cable to be re-tensioned, a non-crimping securing mechanism, and multiple cable orientations.

SUMMARY OF THE INVENTION

An embodiment of the invention relates to a surgical cable system that preferably includes a connector adapted to hold a cable in a loop around a human bone element and a tensioner. The connector may include a connector body, a cable, and a pin adapted to secure the cable within the connector body. The term "cable" within the context of this application is taken to mean an elongated flexible member. The term "pin" within the context of this application is taken to mean an elongated inflexible member.

The connector body preferably includes a first arm and a second arm, an internal cavity, and at least two ducts. The first and second arms preferably extend from the same face of the connector body such that the connector body is substantially U-shaped. The internal cavity preferably runs longitudinally through the entire connector body and passes in between the two arms. The ducts preferably run transversally through the entire connector body, perpendicular to the internal cavity. The ducts are preferably oriented such that the ends of a cable, when the cable is passed through the ducts to form a loop, may be oriented in a substantially parallel orientation with respect to each other. The ducts are preferably located proximate to the internal cavity. The connector body may contain at least one aperture that is positioned between a duct and the internal cavity. The connector body preferably contains two apertures that connect two separate ducts to the internal cavity. The ducts, the apertures, and the internal cavity are oriented with respect to one another such that a cable passing through the duct may extend through the aperture into the internal cavity.

The cable is preferably substantially flexible such that the cable may form a loop for engaging a portion of a human bone. The cable is preferably of a diameter such that the cable may pass freely through a duct. The cable is also preferably of a diameter such that it may extend from the duct, through the aperture, and into the internal cavity. The cable preferably includes a tip which may inhibit the end of the cable from passing through the duct.

The pin includes an upper portion and a lower portion. The upper portion may have a diameter that is substantially larger than the diameter of the internal cavity such that the upper portion of the pin is inhibited from passing through the internal cavity. The lower portion of the pin may have a diameter that is substantially less than the diameter of the internal cavity such that the lower portion of the pin fits within the internal cavity.

The pin may be positionable within the internal cavity where it may exert a compressive force against the cable to secure the cable within the internal cavity. The cable may be looped around a bone and through the ducts. Subsequently, positioning the pin within the connector body may secure the cable in place. While the cable is secured the cable is no longer able to move within the connector. The bottom edge of the pin may be deformed to secure the pin within the internal cavity.

More preferably, the pin is placed within the internal cavity of the connector body before the cable is threaded. The pin may be secured within the internal cavity by deforming the bottom edge of the pin. Removal of the pin may be inhibited by the deformed bottom edge. The pin may be substantially rotatable while positioned within the internal cavity. The upper portion of the pin may contain at least two flat edges, the edges being oriented on opposing sides of the upper portion of the pin. The distance between the two edges may be less than the distance between the two arms extending from the connector body. The arms may interact with the edges such that rotation of the pin is hindered. The pin may be rotatable when sufficient force is applied to overcome the hindering force of the arms.

The pin preferably includes two grooves. The grooves may be aligned with the apertures, when the pin is inserted within the internal cavity, such that the cable may pass freely through the connector body. The pin may also be rotated, while the pin is inserted within the internal cavity, such that the grooves are perpendicular to the apertures. The rotation of the pin, after a cable has been threaded through the connector body, may exert a compressive force against the cable to secure it within the connector body. The pin may be subsequently rotated to allow free movement of the cable through the connector body.

The pin may further include an opening extending longitudinally through the entire pin. The opening preferably includes a top section and a bottom section. The top section preferably has a diameter that is substantially greater than the diameter of the end of the cable. The bottom section preferably has a diameter that is substantially less than the diameter of the tip of the cable. The cable may be passed through the opening, with the tip of the cable positioned within the opening, and further through a duct to form a loop. The pin may be positioned within the internal cavity to secure the cable in place, while the cable is passed through the opening and the duct. When secured in this position the cable may be oriented in a substantially perpendicular orientation.

The cable may be passed through the ducts of the connector body such that the ends of the cable are oriented in a substantially parallel orientation. Alternatively the cable may be passed through the opening of the pin and through a duct to form a loop, the ends of the cable being in a substantially perpendicular orientation.

The surgical cable system may also include a tensioner adapted to vary the tension of the cable and secure the cable. The tensioner preferably includes a body, a shaft for contacting the connector, a driver for positioning the pin within the connector body, and an arm for adjusting the shaft.

The shaft is preferably mounted within the body, such that it extends from both sides of the body. The arm and the shaft are preferably connected such that the arm is capable of being adjusted to retract or extend the shaft from an end of the body. The body may include a stopper which secures the position of the shaft with respect to the body.

The shaft preferably includes a tip adapted to hold the connector. The tip may include a recessed opening which is shaped to couple to the connector. The shaft may also include an opening extending longitudinally through the shaft. The opening of the shaft is preferably adapted to allow the driver to pass through the shaft and onto the connector.

The body may include a cable clamp adapted to secure the cable against a portion of the body. The body preferably includes at least two cable clamps. The cable clamps may secure the cable against a portion of the body after the cable is threaded through the connector and around a portion of a human bone. The shaft may engage the connector, after the cable has been secured with respect to the body, such that movement of the shaft causes the tension of the cable to vary.

The driver may include an end adapted to engage the pin of the connector. The driver preferably includes a handle to allow the driver to be moved in a circular motion. The shaft preferably includes an opening, extending longitudinally through the shaft, that allows the driver to engage the pin while the connector is in contact with the shaft. The driver may engage the pin such that rotation of the driver causes the pin to rotate into a position which secures the cable within the connector. While the cable is secured the cable is no longer able to move within the connector. Subsequent to securing the cable, the driver may be rotated to cause the pin to move into a position which allows the cable to once again have mobility within the connector.

In another embodiment, a protrusion may be built onto the upper portion of a pin. The protrusion is preferably configured to interact with a locking portion built onto the connector body such that the protrusion and the locking portion together inhibit rotation of the pin. The connector body preferably includes a locking portion made up of at least one projection. The locking portion preferably extends along the side of the connector body. The projection preferably includes an opening for receiving the protrusion.

The protrusion is preferably oriented away from the locking portion when the pin is in an unlocked position. When the pin is in an unlocked position the cable may be free to move through the connector. When the pin is in a locking position the cable is preferably inhibited from moving through the connector. In the locked position the pin is positioned such that the protrusion now lies within the opening formed by projections. The flat edge of the protrusion preferably engages the flat edge of the projection to inhibit rotation of the pin.

While rotation of the pin in a first direction is substantially inhibited, the pin may be turned in an opposite direction. When rotated in a first direction, the rounded edge of the protrusion contacts the projection of the locking portion to slightly inhibit the rotation of the pin. Applying sufficient rotational force to the pin may cause the projection to deflect slightly outward, providing sufficient space for the protrusion to be rotated past the projection and away from the locking portion. In this manner the pin may be moved into an unlocked position.

In another embodiment, a connector including two locking portions may be used in conjunction with a pin including two protrusions. The first locking portion of the connector is preferably oriented opposite a second locking portion. The pin preferably includes two protrusions oriented opposite to each other. Each protrusion preferably includes a rounded side and a flat side.

When the cable is to be secured within the connector, the pin may be rotated in a first direction. Rotation in this direction preferably moves the pin into a locking position. When the pin is positioned in this locking orientation the protrusions move into the openings of locking portions. Thus, the action of securing the cable by rotating the pin preferably moves the protrusions into a position such that rotation in a direction opposite to the direction for securing the cable is inhibited.

An advantage of the present invention is that the cable may be secured or movable within the connector as necessary.

Another advantage of the present invention is that the cable may be secured into position without the use of crimps.

Yet another advantage is that the present invention may allow the ends of the cable to be in a perpendicular orientation with respect to each other or a parallel orientation with respect to each other.

The use of two projections and two locking portions has the advantage that the pin may be secured in a locked position whenever the cable is secured within the connector body. Additionally, the two projections may provide increased resistance to rotation of the pin in a clockwise direction when the pin is in a locked position.

BRIEF DESCRIPTION OF THE DRAWINGS

Further advantages of the present invention will become apparent to those skilled in the art with the benefit of the following detailed description of the preferred embodiments and upon reference to the accompanying drawings in which:

FIG. 4 depicts a cross sectional view of a pin as viewed facing a groove from the front face;

FIG. 5 depicts a side view of the pin;

FIG. 6 depicts a cross sectional view of the pin as viewed from the front;

FIG. 10 depicts a cross sectional view of the connector, with the cable being movable within the connector body, as viewed from the side;

FIG. 11 depicts a cross sectional view of the connector, with the cable being secured in an immobile position within the connector, as viewed from the side;

FIG. 12 depicts a cross sectional view of the connector, with the cable being movable within the connector body, as viewed from the bottom;

FIG. 13 depicts a cross sectional view of the connector, with the cable secured in an immobile position within the connector body, as viewed from the bottom

FIG. 17 depicts a cross sectional view of the tensioner, as viewed from the side;

FIG. 18 depicts a tip of a shaft of the tensioner, as viewed from the front;

FIG. 19 depicts the tip of the shaft as viewed from the side;

FIG. 26a depicts a top view of a connector with a pair of locking projections in an unlocked position.

FIG. 26b depicts a top view of a connector with a pair of locking projections in a locked position.

Figure 1:
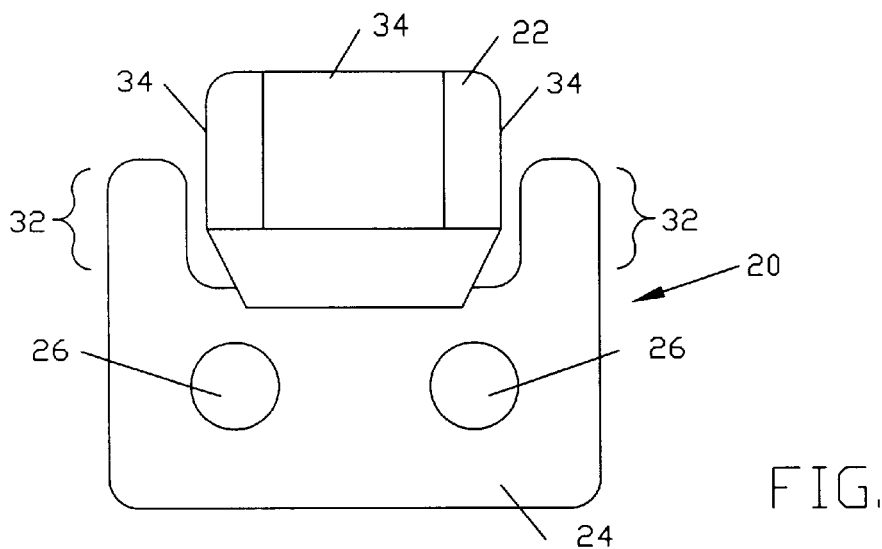
FIG. 1 depicts a side view of a connector.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

FIG. 1 depicts an embodiment of a connector 20 constructed according to the teachings of the present invention. The connector 20 includes a connector body 24 and a pin 22. A cable 10 may be passed through the ducts 26 to form a loop for engaging a portion of a human bone. The cable 10 may be looped around a variety of human bone portions involved in various surgical procedures. The surgical procedures which may make use of a surgical cable system include, but are not limited to: spine surgery; total hip arthroplasty; fracture fixation; closure of the sternum following open heart surgery; and oral/facial surgery to repair mandibular fractures. The cable 10 is preferably used for engaging a portion of the human spine.

Figure 2:
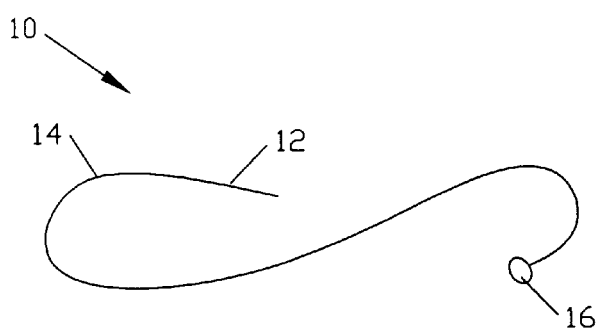
FIG. 2 depicts a perspective view of a cable.

The term "cable" within the context of this application is taken to mean an elongated flexible member. An embodiment of the cable 10 is illustrated in FIG. 2. The cable 10 includes a leader portion 12, a main portion 14, and a tip 16. The main portion 14 is preferably composed of a substantially flexible stranded metal wire. The main portion 14 may be composed of any substantially flexible material including, but not limited to, steel, nylon, or various plastics. The main portion 14 is preferably made of titanium or stainless steel.

The cable 10 preferably has a leader portion 12 attached to an end of the cable. The leader portion 12 may include a non-stranded wire that is substantially less flexible than the main portion 14. The leader portion 12 may be composed of any substantially flexible material including, but not limited to, steel, nylon, or various plastics. The leader portion 12 is preferably made of titanium or stainless steel. The leader portion 12 is preferably made of the same material as the main portion 14 of the cable 10. The leader portion 12 may be used to guide the cable 10 around the bone and through the various openings of the connector 20.

The cable 10 may include a tip 16 attached to an end of the cable. The tip 16 is preferably of a diameter that is substantially larger than the diameter of the main portion 14. The tip 16 may be made of the same material as the main portion. The tip 16 is preferably made of titanium or stainless steel. The tip 16 may be larger than the diameter of the ducts 26, (shown in FIG. 1), such that the tip 16 is inhibited from passing through the ducts. Thus, tip 16 may function to prevent the cable 10 from passing entirely through the ducts 26.

The cable 10 is preferably made by twisting together multiple wire strands around a cable core. The wire strands are preferably made by twisting six filaments around a central filament in a helical orientation. The filaments may be made by reducing the diameter of a wire to a thickness of less than 0.005 inches, and more preferably to a diameter of 0.003 inches. The cable core is preferably made by twisting six wire strands over a central strand in a helical orientation. The cable 10 is preferably made by twisting twelve strands over the cable core. After the strands are twisted to form the cable 10, the cable may be hammered repeatedly to give a smooth surface. The cable 10 may be cut into the appropriate length by a cutting apparatus. The cable 10 is preferably cut by a laser. By applying tension on the cable 10 during the cutting process an end of the cable may be formed into an enlarged tip 16. The leader portion 12 may be welded onto an end of the cable 10 before use. The cable may be cleaned repeatedly during the manufacturing procedure.

Figure 3:
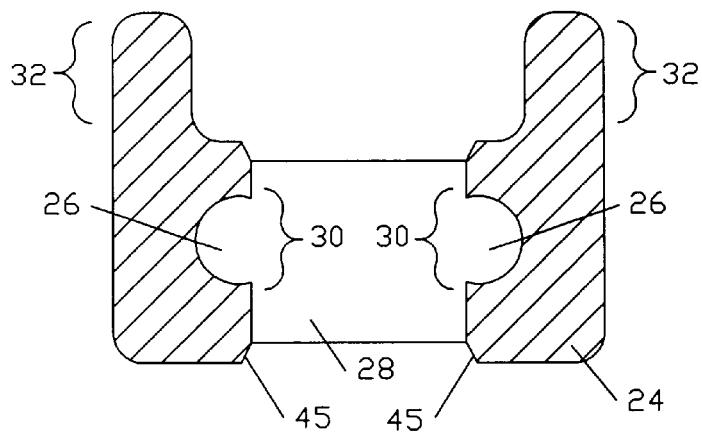
FIG. 3 depicts a cross sectional view of the connector as viewed from the side.

FIG. 3 depicts a cross sectional view of the connector body 24 of the connector 20. The connector body 24 preferably includes an internal cavity 28 for holding a pin 22 within the connector body 24. The internal cavity 28 may be substantially cylindrical in shape and preferably passes longitudinally through the entire connector body 24. The connector body 24 may include a duct 26 that passes transversally through the entire connector body. The duct 26 is preferably oriented substantially perpendicular to the internal cavity 28. The connector body 24 preferably includes at least two ducts 26 that pass transversally through the entire connector body. The ducts 26 preferably communicate with the internal cavity 28 via an aperture 30. The ducts 26 are preferably positioned such that a cable 10 lying within the duct may extend into the internal cavity 28.

The pin 22 preferably includes an upper portion 36 and a lower portion 40, as depicted in FIG. 4. The pin 22 may also include a transition portion 38 oriented between the upper portion 36 and the lower portion 40. The upper portion 36 is preferably of a diameter substantially larger than the diameter of the lower portion 40. The upper portion 36 is preferably of a diameter such that it is incapable of passing into the internal cavity 28. The lower portion 40 of the pin 22 is preferably of a diameter such that the lower portion may fit into the internal cavity 28 (shown in FIG. 2). The diameter of the transition portion 38 may be variable, becoming narrower in a direction from the upper portion 36 toward the lower portion 40. The bottom of the pin 43 may be deflected outward to substantially secure the pin 22 within the internal cavity 28.

Figure 9:
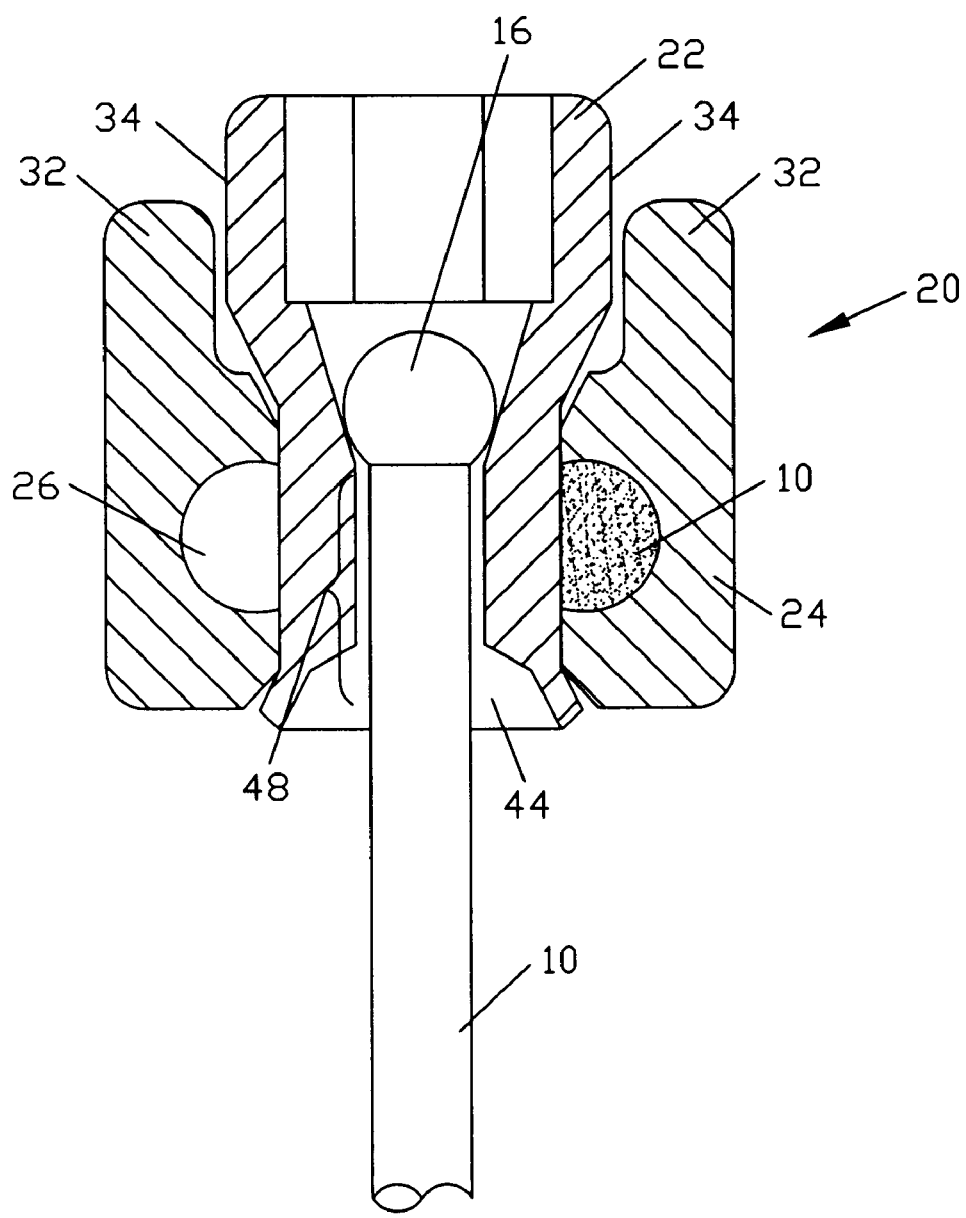
FIG. 9 depicts a cross sectional view of the connector in a secured position, with a portion of the cable residing in an opening of the pin, as viewed from the side of the connector.

In another embodiment, the pin 22 preferably includes two grooves 42, as depicted in FIG. 5. The grooves 42 may be substantially rectangular in shape, having a width that is substantially larger than the diameter of the cable 10. The grooves 42 are preferably oriented on opposing sides of the lower portion 40 of the pin 22. Referring to FIG. 9, the pin 22 may lie within the internal cavity 28 such that the grooves 42 lie in the plane defined by the ducts 26. The grooves 42 may be substantially aligned with the ducts 26, with an aperture 30 positioned between each duct and groove. The pin 22 may be oriented within the internal cavity 28, with the grooves 42 substantially aligned with the ducts 26, such that the cable 10 may pass freely through the connector body 24. The pin 22 may also be oriented within the internal cavity 28, with the grooves 42 positioned substantially perpendicular to the ducts 26, such that the cable 10 is secured within the connector body 24.

In another embodiment, the pin 22 preferably includes an opening 44, as depicted in FIG. 6. The opening 44 is preferably substantially cylindrical in shape and preferably passes longitudinally through the entire pin 22. The pin may surround a portion of the opening such that the opening is U-shaped or V-shaped. The pin preferably surrounds the entire opening. The opening 44 preferably includes an upper portion 46 and a lower portion 48. The pin 22 may also include a transition portion 47 oriented between the upper potion 46 and the lower portion 48. The upper portion 46 is preferably of a diameter substantially larger than the diameter of the lower portion 48. The diameter of the upper portion 46 is preferably substantially larger than the diameter of the tip 16 of cable 10. The diameter of the lower portion 48 is preferably substantially smaller than the diameter of the tip 16 of cable 10. In this manner, the opening 44 may prevent a cable 10, having a tip 16, from passing completely through the opening.

The upper portion 46 of the opening 44 may be chosen to couple with any suitable device adapted to apply a torsional force. The upper portion 46 may be substantially rectangular for receiving a flat head torsioning device, such as a screw driver. The upper portion 46 may also be substantially cross shaped for receiving a cross shaped head of a torsioning device, such as a Phillips head screwdriver. The upper portion 46 is preferably hexagonal in shape for receiving a hexagonal head of a torsioning device, such as an Allen wrench.

Figure 7:
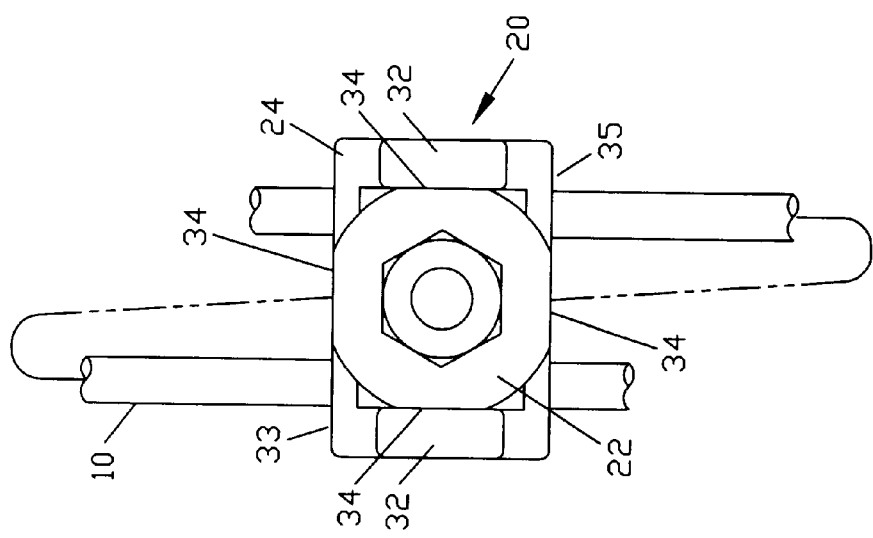
FIG. 7 depicts a top view of the connector with the cable forming a loop by entering a first face opposite to a second face from which it exits.

FIG. 7 depicts a connector 20 with a cable 10 threaded through the connector body 24 to form a loop according to one embodiment. The cable 10 is preferably threaded through a duct 26, around a human bone element, and back through a separate duct 26 to form a loop. The loop is formed such that the ends of the cable 10 lie in a substantially parallel orientation with respect to each other. The cable 10 is preferably threaded through a duct 26, around a human bone element, and back through another duct to form a loop, reentering the connector body 24 from the face 35 on the side opposite to the face 33 which the cable initially exited. The pin 22 may be inserted within the connector body 24, after the cable 10 has been looped around a human bone element and passed through the connector body 24 to secure the cable within the connector body. The pin 22 may be removed from the connector body 24, subsequent to securing the cable 10 within the connector body, to allow the cable to be moved within the connector body. Removal of the pin 22 may be prevented by deforming the bottom of the pin.

Figure 8:
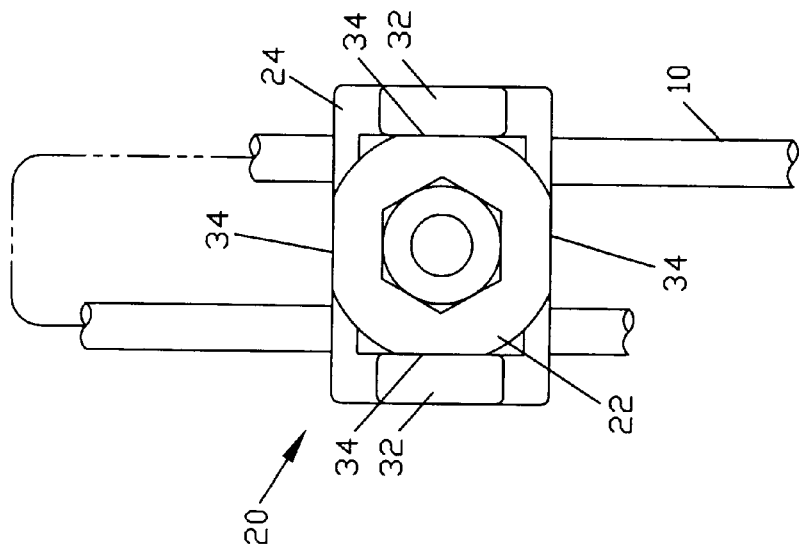
FIG. 8 depicts a top view of a connector with the cable forming a loop by entering the same face from which it exits.

FIG. 8 depicts another embodiment in which the cable 10 is preferably threaded through a duct 26, around a human bone element, and back through a separate duct to form a loop, reentering the connector body 24 from the same face 33 of the connector body that the cable initially exited. The pin 22 may be inserted within the connector body 24 to secure the cable 10 within the connector body. While the cable 10 is secured the cable is no longer able to move within the connector 20. The pin 22 may be removed from the connector body 24, subsequent to securing the cable 10 within the connector body, to allow the cable to be moved within the connector body.

FIG. 9 depicts another embodiment in which the cable 10 is preferably threaded through the opening 44, around a human bone element, and back through a duct 26 to form a loop. In this manner, the ends of the cable 10 may lie in a substantially perpendicular orientation with respect to each other (not shown). The pin 22 may be inserted within the connector body 24 to secure the cable 10 within the connector body. The pin 22 may be removed from the connector body 24, subsequent to securing the cable 10 within the connector body, to allow the cable to be movable within the connector body. Tension on the cable 10 may pull the tip 16 of the cable against the lower portion 48 of the opening 44. In this manner, the cable 10 may be prevented from moving within the opening 44.

The pin 22 may be positioned within the internal cavity 28 before the cable 10 is threaded through the ducts 26. The cable 10 may be threaded through the ducts 26 of the connector body 24 while the pin 22 is mounted within the internal cavity 28. The pin 22 is preferably oriented such that the grooves 42 of the pin are substantially aligned with the ducts 26, as depicted in FIGS. 10 and 12. The pin 22 may be rotated, subsequent to the cable 10 being passed through the connector body 24, such that the grooves 42 are substantially perpendicular to the ducts 26. As a result, the ungrooved portion of the pin 22 may compress the cable 10 against the connector body 24, securing the cable, as depicted in FIGS. 11 and 13. Subsequent to securing the cable 10 within the connector body 24, the pin 22 may be further rotated such that the grooves 42 are once again aligned with the ducts 26. In this manner, the cable 10 may be repeatedly moved and secured within the connector body 24.

In another embodiment, the cable 10 may be threaded through the pin 22 and through a duct 26 of the connector body 24, as depicted in FIG. 9. The pin 22 may be rotated within the connector body 24 to secure the cable 10 in an immobile position within the connector body. Subsequent to securing the cable 10 in an immobile position within the connector body 24, the pin 22 may be further rotated such that the cable may again be movable within the connector body. Tension on the cable 10 may pull the tip 16 of the cable against the lower portion 48 of the opening 44. In this manner, the cable 10 may be prevented from moving within the opening 44.

The connector body 24 preferably has two substantially flat arms 32 extending out from the top face of the connector body, as depicted in FIG. 9. The arms 32 are preferably oriented opposite to each other, and the internal cavity 28 is preferably located between the two arms. The upper portion 36 of the pin 22 may have at least two substantially flat edges 34. The upper portion 36 of the pin 22 more preferably has four substantially flat edges 34 (shown in FIG. 7). The edges 34 are preferably oriented on opposing sides of the upper portion 36 of the pin 22. The pin 22 may be mounted within the internal cavity 28 such that the edges 34 are contained by the arms 32 of the connector body 24. The arms 32 may interact with the edges 34 such that rotation of the pin 22 is hindered. The pin 22 may be rotatable when sufficient force is applied to the pin to overcome the hindering force of the arms 32.

As illustrated in FIG. 10 the pin 22 may be inserted within the internal cavity 28 and the pin bottom 43 deflected outward. The diameter of the bottom 45 of the internal cavity 28 is preferably tapered, becoming wider in a direction toward the bottom 45 of the connector body 24. The deflection of the bottom 43 of pin 22 is tapered to match the tapering of the internal cavity 28. The pin 22 is preferably rotatable within the internal cavity 28. The lower portion 40 of the pin 22 is preferably of a diameter such that, when positioned within the internal cavity 28, the lower portion may compress the cable 10 against the wall of the duct 26, securing the cable in place.

The cable 10 is preferably formed into a loop and tensioned prior to securing the cable within the connector body 24. When the cable 10 is under tension, the corners of the edge 34 of the pin 22 may rest upon the inner faces of the arms 32. The force exerted by the arms 32 upon the corners of the edges 34 may prevent the pin 22 from rotating due to the tension of the cable 10. The pin 22, however, may be rotated by an operator to a position which allows the cable 10 to be movable through the connector body 24. The force required by the operator to move the pin 22 into an unsecured position is preferably greater than the rotational force exerted on the pin by the cable 10 when in a secured position.

Figure 14:
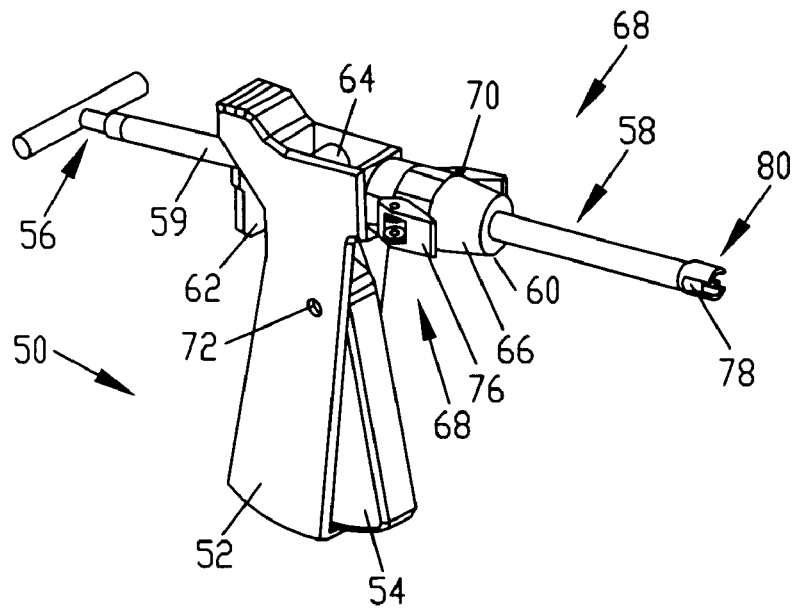
FIG. 14 depicts a perspective view of a tensioner.

The surgical cable system preferably includes a tensioner 50 adapted to vary the tension of the cable 10 and secure the cable within the connector 20. An embodiment of the tensioner 50 is depicted in FIG. 14. The tensioner 50 preferably includes a body 52, a shaft 58 for contacting the connector 20, a driver 56 for positioning the pin 22 within the connector 20, and an arm 54 for adjusting the position of the shaft 58. The parts of the tensioner 50 may be made of a variety of substantially inflexible materials including, but not limited to, instrument grade stainless steel, aluminum, and various plastics.

Figures 15, 16:
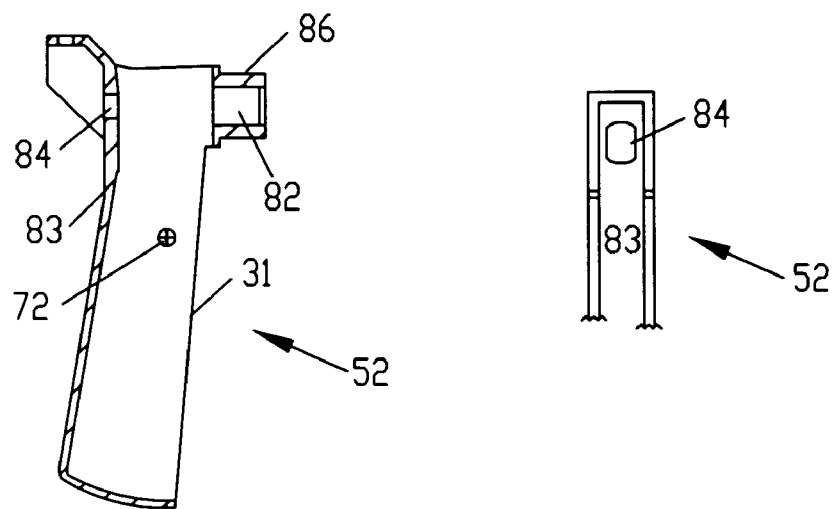
FIG. 15 depicts a cross sectional view of a body of the tensioner, as viewed from the side.
FIG. 16 depicts a rear view of the body of the tensioner.

FIG. 15 depicts a cross sectional side view of the body 52. The body 52 is preferably substantially rectangular and hollow. The body 52 preferably includes a substantially circular front opening 82 and a substantially oval rear opening 84. The body 52 may also include a bushing holder 86 extending from the front edge 81 of the body. The front opening 82 may pass through the bushing holder 86. The front opening 82 and the rear opening 84 may be aligned such that a rigid, elongated member may be passed through both openings. The front edge 81 of the body 52 may be uncovered allowing insertion of the arm 54 within the body.

FIG. 16 depicts an embodiment of the rear opening 84 of the body 52. The rear opening 84 preferably includes two curved sections and two flat sections. The curved sections may be oriented at the top and the bottom of the rear opening 84. The flat sections may connect the top curved section to the bottom curved section to form a substantially oval opening.

The arm 54 may be substantially hollow and is preferably mounted within the hollow portion of the body 52, as depicted in FIG. 17. The arm 54 may be held in place by the arm pin 72. The arm pin 72 may be substantially cylindrical and hollow. The arm pin 72 may extend through the entire arm 54 and partially into the sides of the body 52. The arm pin 72 may be mounted within the body 52 such that the arm 54 is pivotable about the arm pin in a range of about 45 degrees. The arm 54 may be stopped in a forward position when the top 53 of the arm comes into contact with the body 52, as depicted in FIG. 17. The arm 54 may be similarly stopped in a rear position when the bottom 55 of the arm 54 comes into contact with the body 52. The sides of the arm 54 preferably extend above the top of the arm to form a substantially U-shaped pocket. The U-shaped pocket may be adapted to hold a push tab pin 88 that may be mounted over the top of the arm 54 extending into the sides of the arm.

Turning to FIG. 17, the push tab 64 may be substantially rectangular. The push tab 64 preferably includes a substantially circular aperture. The push tab 64 may rest on the front portion of the push tab pin 88. The aperture of the push tab 64 is preferably sized such that the shaft 58 may be passed through the aperture. The push tab 64 is preferably placed within the hollow portion of the body 52. The shaft 58 is preferably fitted through the aperture of the push tab 64, and the lower portion of the push tab is preferably seated against the push tab pin 88. The arm spring 92 may also lie on the shaft 58, preferably positioned between the push tab 64 and the front 81 of the body 52.

The arm 54 is preferably pivotable about the arm pin 72 such that a bottom portion 55 of the arm may be moved toward the rear 83 of the body 52. Rearward motion of the arm 54 preferably causes the push tab pin 88 to move toward the front 81 of the body 52. Push tab 64 preferably rests against the push tab pin 88. Thus, movement of the push tab 64 toward the front 81 preferably makes the push tab pin 88 move in a similar direction. As a result, the push tab 64 may engage the shaft 58, propelling the shaft through the front opening 81 of the body 52. Concurrent with the movement of the arm 54, the push tab 64 may also compress the arm spring 92. In the absence of any pressure on arm 54, the arm spring 92 preferably expands such that the push tab 64, the push tab pin 88, and the arm 54 are returned to their original positions.

The body 52 may further include a lock tab 62 and lock spring 94. The lock tab 62 may be substantially rectangular. The lock tab 62 preferably includes a substantially circular aperture. The lock tab 62 may extend downward from the top of the body 52, as depicted in FIG. 17. The aperture is preferably sized such that the shaft 58 may be passed through the aperture. The lock spring 94 may also lie on the shaft 58, preferably positioned between the lock tab 62 and the body 52. The lock spring 94 preferably exerts a force on the lock tab 62, forcing it away from the rear 83 of the body 52. Movement of the lock tab 62 in this direction is preferably restricted when the lower portion of the aperture comes into contact with the shaft 58. The force exerted by the lock tab 62 upon the shaft 58 may restrict the rearward motion of the shaft through the body 52.

The lock tab 62 may be moved toward the front 81 of the body 52 such that the aperture no longer comes into contact with the shaft 58. When oriented in this forward position the lock tab 62 may no longer restrict the rearward motion of the shaft 58. The lock tab 62 is preferably moved into the forward position to allow the shaft 58 to be moved in a rearward direction within the body 52. Movement of the lock tab 62 toward the front of the body 52 may also compress the lock spring 94. When the pressure being applied to the lock tab 62 is released, the lock spring 94 preferably pushes the lock tab 62 back into its starting position.

The shaft 58 may be a variety of shapes including, but not limited to cylindrical, oval or trapezoidal. The shaft 58 is preferably substantially cylindrical and hollow. The shaft 58 may include two flat edges 59 (shown in FIG. 14) that run longitudinally along the entire length of the shaft 58. The edges 59 are preferably oriented on opposing sides of the shaft 58, giving the shaft a substantially oval shape. Referring back to FIG. 16, the rear opening 84 of the body 52 is preferably shaped to allow a shaft 58 of complimentary shape to pass through the rear opening. The rear opening 84 is preferably shaped to inhibit rotation of the shaft 58 within the body 52. The width of the hollow portion of the shaft 58 is slightly greater than the diameter of the driver 56, thereby allowing the driver to freely pass through the shaft. The shaft 58 may also include a knob 96 at an end of the shaft, as depicted in FIG. 17. The knob 96 may be a threaded nut which is screwed onto the shaft 58. The knob 96 may be used to position the shaft 58 within the body 52.

The shaft 58 preferably includes a tip 80 proximate an end of the shaft which is adapted to hold the connector 20. The tip 80 is preferably located at the end of the shaft 58 which extends from the front 81 of the body 52. FIG. 18 depicts an embodiment of the tip 80. The tip 80 may be slightly larger than the diameter of the shaft 58. The tip 80 preferably includes two indentations 78 running along the outside surface of the tip. The indentations 78 are preferably oriented on opposing sides of the tip 80. The indentations 78 are preferably sized such that the width of the indentations are substantially greater than the width of the cable 10. The depth of the indentations 78 is preferably tapered, becoming shallower in a direction from the end of the shaft 58 toward the body 52.

The tip 80 may include a recessed opening which is adapted to couple with the connector 20. The front of the tip 80 is depicted in FIG. 19. The front of the tip 80 preferably contains a first slot 96 and a second slot 98. The first slot 96 preferably runs across the end of the tip 80, in the plane of the tip 80 formed by the two indentations 78. The second slot 98 preferably runs in a substantially perpendicular orientation to the first slot 96. The depth of the second slot 98 may be substantially greater than the depth of the first slot 96. The connector 20 may be mounted within the tip 80 such that the ducts 26 are oriented toward the indentations 78 of the tip. This arrangement preferably allows the cable 10 to freely pass through the connector 20 and along the indentations 78 while the connector 20 is mounted within the tip 80.

Figure 20:
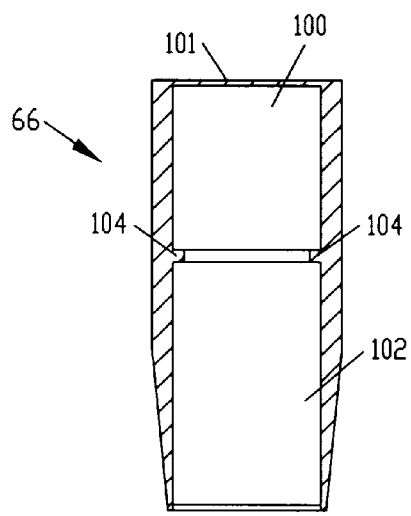
FIG. 20 depicts a cross-sectional view of a bushing cover of the tensioner as viewed from the side of the bushing cover.
Figure 21:
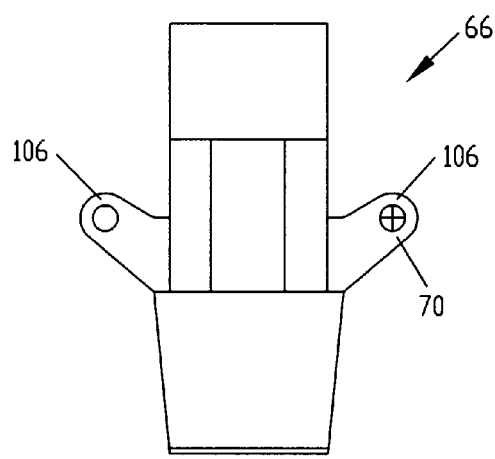
FIG. 21 depicts a side view of the bushing cover.
Figure 22:
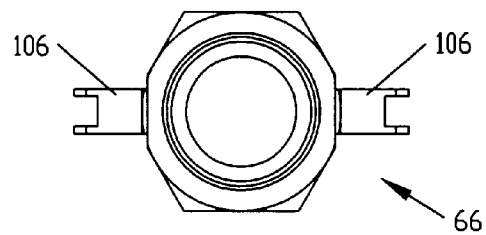
FIG. 22 depicts a top view of the bushing cover.

The body 52 may also include a substantially cylindrical and hollow bushing cover 66, as depicted in FIGS. 20, 21, and 22. The bushing cover 66 preferably includes an upper chamber 100, a lower chamber 102, a divider 104 and two arms 106. The upper chamber 100 is preferably sized such that the bushing cover 66 may be inserted over the bushing holder 86, as depicted in FIG. 17. The distance between the divider 104 and the top 101 of the bushing cover 66 may be substantially less than the distance that bushing holder 86 extends out from the body 52. The distance is set such that a space may exist between the bushing cover 66 and the front edge 81 of the body 52. The divider 104 preferably extends partially into the interior of the bushing cover 66, at a distance allowing the shaft 58 to pass through the bushing cover. The lower chamber 102 is preferably sized to allow the bushing 60 and the bushing spring 90 to be inserted together within the chamber, as depicted in FIG. 17. The arms 106 preferably extend from opposing sides of the bushing cover 66. The end of each arm 106 is preferably shaped into a substantially U-shaped groove, as depicted in FIG. 22. The bushing spring 90 is preferably sized to fit within the lower chamber 102. The bushing spring 90 is preferably sized to fit over the bushing 60.

Referring back to FIG. 17, the body 52 may include a substantially cylindrical and hollow bushing 60. It is preferred that the width of the hollow portion of the bushing 60 and the diameter of the shaft 58 be substantially equal. The shape of the hollow portion is preferably complimentary to the shape of the shaft 58. The hollow section may extend through the longitudinal axis of the bushing 60. The bushing 60 is preferably mounted within the bushing holder 86. The engagement of the bushing 60 with the shaft 58, while the bushing 60 is mounted within the bushing holder 86, preferably minimizes the lateral movement of the shaft within the body 52. The bushing holder 86 preferably contains female threading. The bushing 60 may include a threaded end, sized to fit the female threading of the bushing holder 86. The threaded end of the bushing 60 preferably engages the bushing holder 86 such that rotation of the bushing in a tightening direction moves the threaded end into the bushing holder.

The bushing 60 is preferably adapted to hold the bushing cover 66 onto the bushing holder 86, whereby the bushing cover is freely rotatable about the bushing holder. The bushing 60 preferably includes a flanged end. The bushing cover 66 and the bushing spring 90 are preferably placed on the bushing holder 86, such that the bushing spring lies within the lower chamber 102 of the bushing cover. The bushing spring 90 may rest against a front edge of the bushing holder 86. The bushing 60 may be fastened by screwing the threaded end into the threaded portion of the bushing holder 86. The flanged end of the bushing 60 preferably presses against the bushing cover 66 to hold the bushing cover against the bushing holder 86. The flanged end of the bushing 60 may also compress the bushing spring 90. The bushing spring 90 is adapted to prevent the bushing 60 from being overtightened. Overtightening of the bushing 60 might hinder or prevent rotation of the bushing cover 66 about the bushing holder 86.

Figure 23:
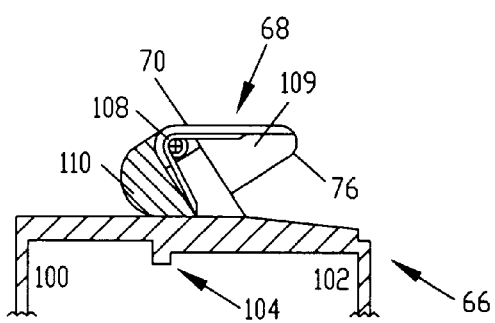
FIG. 23 depicts a cross sectional partial view of the bushing cover with a cable clamp, as viewed from the side.

FIG. 23 depicts a portion of the bushing cover 66 which preferably includes a cable clamp 68 adapted to secure a cable 10 against a portion of the bushing cover. The bushing cover 66 preferably includes at least two cable clamps 68. The cable clamp 68 preferably includes a lever 76, a pin 70, and a spring 108. The lever 76 may include a substantially hollowed out portion 109 and a clamping portion 110. The lever 76 is preferably connected to an arm 106 of the bushing cover 66 with a substantially cylindrical pin 70. The pin 70 may extend through both the lever 76 and the U-shaped groove of the arm 106. The pin 70 may be mounted within the U-shaped groove of the arm 106 such that the lever 76 is pivotable about the pin.

The spring 108 preferably lies on the pin 70 and extends into the bushing cover 66 and along the lever 76. The spring 108 preferably extends into the hollow portion of the lever 76. In its resting position spring 108 preferably exerts a force against the inside edge of the hollow portion 109 such that the lever 76 is moved away from the bushing cover 66. When the hollow portion 109 extends away from the bushing cover 66, the clamping portion 110 is preferably disposed against the bushing cover. When pressed with sufficient force the lever 76 may pivot around the pin 70 such that the clamping portion 110 is no longer in contact with the bushing cover 66. The cable 10 may be passed under the lever 76 while the clamping portion 110 is in its raised position. The depression of the clamp lever 76 preferably compresses the spring 108. Removal of the force being applied to the lever 76 preferably allows the spring 108 to expand, thereby forcing the clamping portion 110 to return to the bushing cover 66. If a cable 10 is present when the force is released from the lever 76, the clamping portion 110 may become pressed against the cable, securing it in place against the bushing cover 66.

The arm spring 92 and the lock spring 94 may be compression springs. The spring 108 of the cable lock 68 is preferably a torsion spring. The bushing spring 90 is preferably a spring washer. The term "spring washer" in the context of this application is meant to mean a spring adapted to apply a predetermined force on adjacent members in an assembly.

Referring back to FIG. 17, the driver 56 may include a handle 114 attached to the elongated member 112 of the driver. The handle 114 is preferably a rod that is attached to the elongated member 112 in a perpendicular orientation, such that the driver 56 is substantially T-shaped. The handle 114 may be rotated to allow the driver 56 to be moved in tortionally. The elongated member 112 may be substantially longer than the shaft 58. The driver 56 preferably includes a head 116 adapted to engage the pin 22 of the connector 20. The head 116 is preferably located at an end of the elongated member 112 opposite to the handle 114. The shape of head 116 may be chosen to couple with a pin 22 of suitably recessed shape such that rotation of the handle may apply a tortional force to the pin. The head 116 is preferably hexagonal in shape for coupling with the hexagonal recess of the upper portion 46 of the opening 44 of the pin 22.

The shaft 58 may be substantially cylindrical and hollow. The hollow portion of the shaft 58 is preferably sized such that the elongated portion 112 of the driver 56 may be passed through the center of the shaft. The shaft 58 is configured such that the driver 56 may engage the pin 22 while the connector 20 is in contact with the shaft. The driver 56 may engage the pin 22 such that rotation of the driver 56 causes the pin to rotate. The driver 56 preferably engages the pin 22 such that rotation of the driver causes the pin 22 to rotate into a position which secures the cable 10 within the connector 20. Once the cable 10 has been clamped into this position, the driver 56 may engage the pin 22 such that rotation of the driver causes the pin to rotate into a position which allows movement of the cable within the connector 20.

The surgical procedure for implanting a surgical cable system around a portion of a human bone includes forming a loop around the desired portion, tensioning the cable 10, and securing the cable within the connector 20. The loop is preferably formed by threading the cable 10 through the connector 20, around a portion of the human bone and back through the connector. In an embodiment, the cable 10 may be looped around two or more adjacent vertebra. In another embodiment the cable 10 may be passed around a vertebra and a spinal fixation device. The spinal fixation device is adapted to immobilize a section of the human spine and may be a rod.

As depicted in FIG. 7, the cable 10 may be passed through a duct 26 of the connector 20, around a portion of the human bone, and back through a different duct 26. In an embodiment, the cable 10 may be threaded through the connector 20 exiting from the rear face 33 of the connector body 24. After encircling a bone member the cable 10 may reenter the connector body 24 from the front face 35. In another embodiment, depicted in FIG. 8, the cable 10 may be threaded through the connector 20 exiting from the rear face 33 of the connector body 24. After encircling a bone member the cable 10 may reenter the connector body 24 from the rear face 33, forming a loop around the bone member. The ends of the cable 10 may extend out from the connector body 24. The ends may be in a substantially parallel orientation with respect to each other.

In another embodiment, the cable 10 may include tip 16, as depicted in FIG. 2. Referring again to FIG. 7, the tip 16 is preferably of a diameter that is substantially larger than the diameter of a duct 26. The tip 16 preferably inhibits the cable 10 from passing completely through the duct 26. The cable 10 may be threaded through the connector 20, exiting from the rear face 33 of the connector body 24. The cable 10 is preferably threaded through the connector body 24 until the tip 16 is disposed against the front face 35 of the connector body 24. After encircling a bone member, the cable 10 may reenter the connector body 24 from the front face 35. In another embodiment, the cable 10 may reenter the connector body 24 from the rear face 33 of the connector body. As the cable 10 is tensioned, the tip 16 may be disposed against the front face 35 of the connector body 24. The tip 16 may remain disposed against the face of the connector body 24 until the tension of the cable 10 is released.

In an alternate embodiment, (referring to FIG. 9) the tip 16 is preferably of a diameter that is substantially larger than the diameter of an opening 44 of pin 22. The tip 16 preferably inhibits the cable 10 from passing completely through the opening 44. The cable 10 is preferably threaded through the opening 44 until the tip 16 is disposed against the lower portion 48 of the opening. After encircling a human bone member, the cable 10 may be passed into the connector body 24 through one of the ducts 26. The pin 22 is preferably oriented to allow this passage of the cable 10 through one of the ducts 26. As the cable 10 is tensioned, the tip 16 may be disposed against lower portion 48 of the opening 44. The tip 16 may remain disposed against the lower portion 48 of the opening 44 until the tension of the cable 10 is released.

A tensioner 50 may be used to increase the tension on a cable 10 after it has been encircled around a human bone member. An embodiment of the tensioner 50 is illustrated in FIG. 14. The tensioner 50 may be prepared to receive the connector 20 by positioning the shaft 58 such that the tip 80 is positioned proximate to the front of the bushing 60. The shaft 58 may be positionable within the body 52 while the lock tab 62 is in a forward position. The lock tab 62 may be moved into the forward position by applying pressure to the rear face of the lock tab 62. Pressure on the lock tab 62 may be released allowing the lock tab to move away from the tensioner body 52. In this released position the lock tab 62 may prevent the rearward movement of the shaft 58.

After the cable 10 is looped around a human bone member and through the connector 20, the connector may be engaged by the tip 80 of the tensioner 50. The connector 20 is engaged by the tip 80 such that the front and rear faces of the connector are aligned with the indentations 78 (see FIG. 19). The top of the connector 20 may be substantially positioned within the tip 80. The pin 22 may be mounted within the connector body 24, and the connector body may be engaged by the tip 80.

A cable end is preferably positioned along the indentations 78 of the tip 80. The cable end is preferably clamped to the tensioner 50 by the cable clamp 68. The clamping portion 110 of the cable clamp 68 may be disposed against the side of the bushing cover 66 while in the resting position. When pressed with sufficient force the lever 76 may pivot around the arm pin 72 such that the clamping portion 110 is no longer in contact with the bushing cover 66. The cable 10 may be passed under the lever 76 while the clamping portion 110 is raised. Removal of the force being applied to the lever 76 preferably causes the clamping portion 110 to move toward the bushing cover 66. As a result, the clamping portion 110 may become pressed against the cable, thereby securing it in place against the bushing cover 66. In an embodiment, one end of the cable 10 is preferably secured to the bushing cover 66, using the cable clamps 68. In another embodiment, both ends of the cable 10 are preferably secured to the bushing cover 66.

Pressure may then be applied to the arm 54 of the tensioner 50 to pivot the arm around the arm pin 72 such that the arm moves in a direction toward the body 52 of the tensioner 50. Movement of the arm 54 toward the body 52 may be accompanied by movement of the shaft 58 away from the body 52. The angle to which the arm 54 is pivoted may determine the distance the shaft 58 extends from the body 52. When the pressure on the arm 54 is released, the arm preferably moves away from the body 52. Movement of the arm 54 away from the body 52 preferably does not effect the position of the shaft 58. With the cable 10 secured to the tensioner 50, movement of the shaft 58 away from the body 52 preferably pulls the cable 10 through the connector 20 in a direction away from the connector. As a result, the tension on the cable 10 preferably increases. The arm 54 may be repeatedly pressured and released as many times as necessary to achieve the desired tension.

In one embodiment, a pin 22 may be inserted into the connector body 24, after the cable 10 has been tensioned, to secure the cable within the connector 20. The driver 56 may be used to insert the pin 22 into the connector body 24. In an alternate embodiment, the pin 22 may be placed in the connector body 24 prior to tensioning the cable 10. The pin 22 may be positioned within the tip 80. The driver 56 may be inserted through the center of the shaft 58 until it engages the pin 22. The end of the driver 56 is preferably shaped to fit within the opening 44 of the pin 22. The rotation of the driver 56 may be accompanied by rotation of the pin 22 while the driver is inserted within the opening 44. The pin 22 is preferably oriented such that the cable 10 may pass through one of the ducts 26. Rotation of the pin 22 may alter the orientation of the pin such that the pin secures a portion of the cable 10 within the connector body 24. The pin 22 is preferably rotated 90° into a securing orientation. Rotation of the pin 22 is preferably performed after the cable 10 has been tensioned. In this manner, the driver 56 may rotate the pin 22 to secure a portion of the cable 10 within the connector 20 without removing the connector from the tip 80.

After securing the cable 10 within the connector 20 the tensioner 50 may be disengaged from the connector. The cable 10 may be removed from the cable clamp 68 before disengaging the tensioner 50. To remove the cable 10, pressure may be applied to the lever 76, causing the lever to lift from the bushing cover 66. As a result, the securing force exerted by the clamping portion 110 is removed, allowing the cable 10 to be removed from under the clamping portion. After removal of the cable 10 from the cable clamps 68, the connector 20 may then be removed from the tip 80 of the tensioner 50.

In an embodiment, the cable 10 may need to be retensioned after the connector 20 has been removed from the tensioner 50. In this situation, the connector 20 may be reinserted into the tip 80 of the tensioner 50. The cable 10 may be secured against the tensioner 50 with the cable clamp 68 of the tensioner 50. The driver 56 may be inserted into the opening 44 of the pin 22. Under these circumstances the pin 22 may be rotated by the driver 56 to an orientation which allows movement of the cable 10 through the connector body 24. The cable 10 may be retensioned by operation of the tensioner arm 54. When the desired tension is achieved, the cable 10 may be secured by the rotation of the pin 22 within the connector 20.

FURTHER IMPROVEMENTS

Referring back to FIGS. 10 and 11, the cable 10 may be secured within the connector when the sides of the pin 22 exert a force against the cable forcing the cable against the sides of the duct 26. The grooves 42 on the lower portion of the pin (shown in FIG. 10) are preferably oriented perpendicular to the cable in this locked position. This force may inhibit movement of the cable 10 through the connector. During typical usage force may be exerted on the cable causing the cable to be pulled in a direction away from the connector. This force may cause the pin to rotate to a position where the grooves are parallel to the cable, thus allowing movement of the cable through the connector body. This rotation is typically inhibited by the upper portion of the pin 22 contacting the arms 32 of the connector. This contact inhibits rotation of the pin, and thus the tension of the system is maintained. Under conditions of extreme tension the resistance to rotation imparted by the arms 32 on the upper portion of the pin 22 may be insufficient to prevent rotation of the pin and loosening of the cable. It is therefore desirable that a system be devised which will prevent rotation of the pin during extreme tension.

Figure 24A:
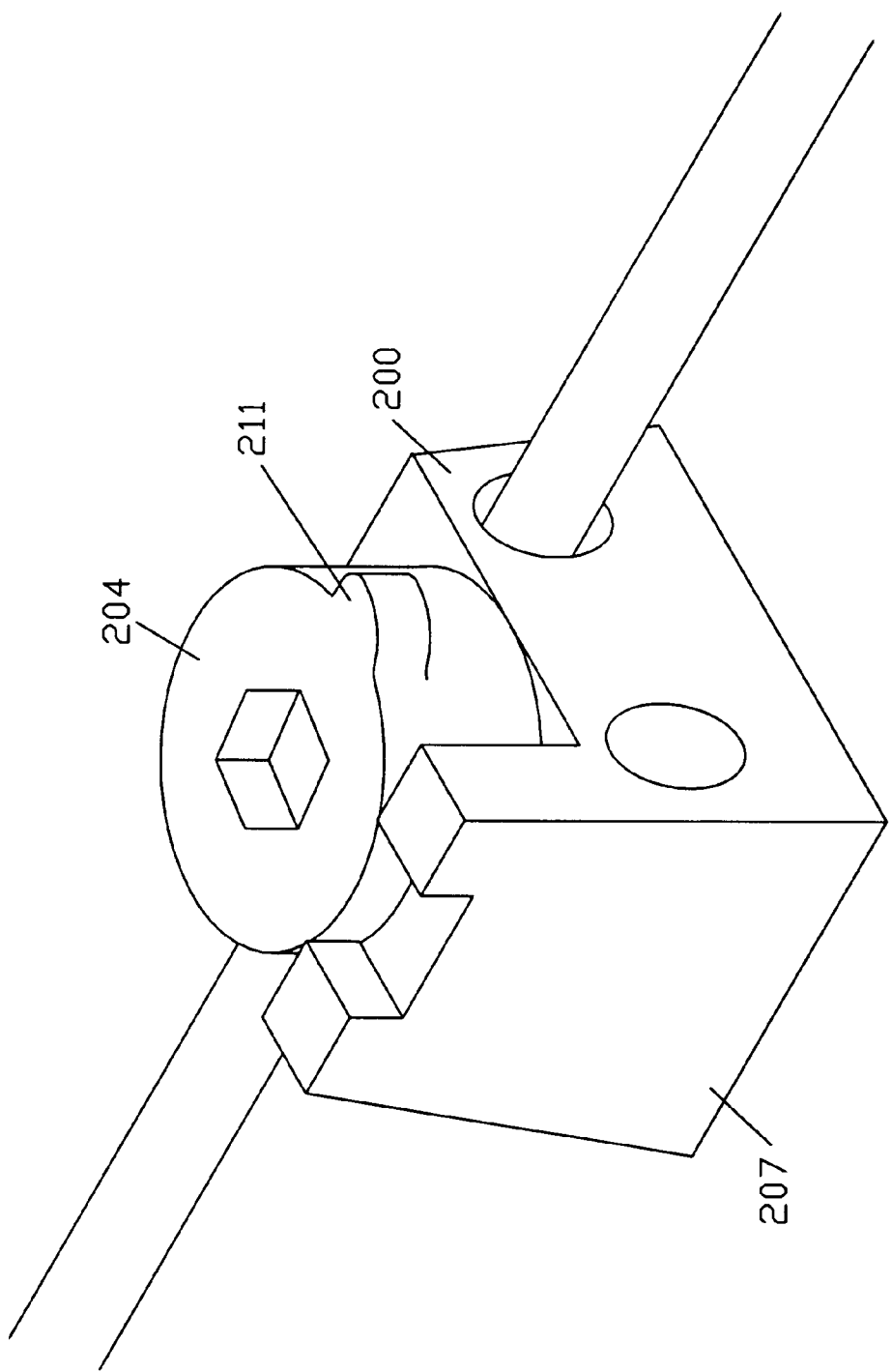
FIG. 24a depicts a perspective view of a connector with a single locking projection.

In one embodiment, a protrusion may be built onto the upper portion of a pin. The protrusion is preferably configured to interact with a locking portion built onto the connector body such that the protrusion and the locking portion together inhibit rotation of the pin. An embodiment of such a system is depicted in a perspective view in FIG. 24a. The system includes a connector body 200 and a pin 204. The connector body preferably includes a locking portion 207 made up of at least one projection. The locking portion 207 preferably extends along the side of the connector body 200. The projection preferably includes an opening for receiving the protrusion 211 formed on the upper portion of the pin 204. The opening may be a hole formed through a portion of the projection. Preferably, the opening may be a slot or indentation formed in the projection (as shown in FIG. 24a).

Figure 24B:
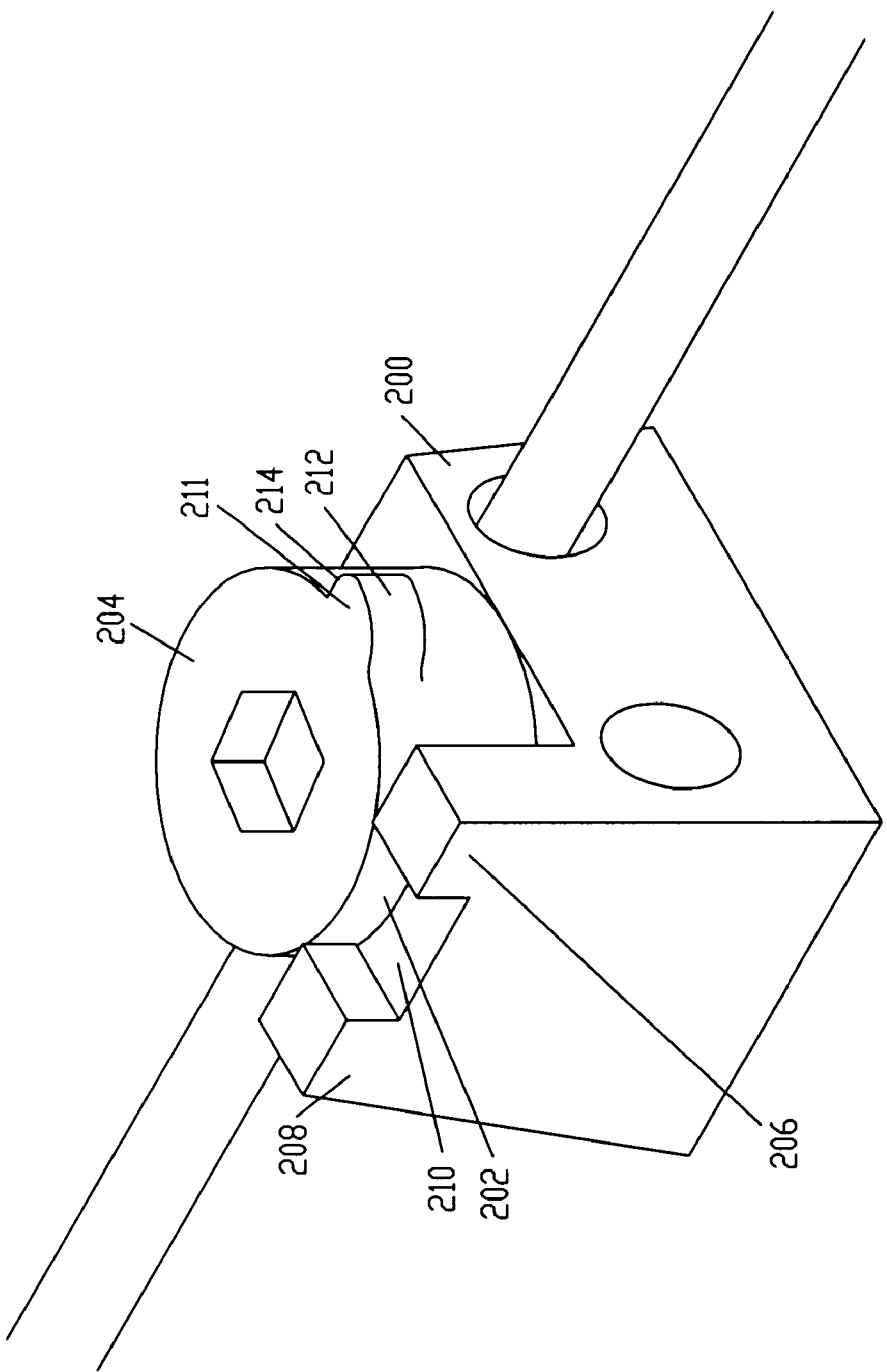
FIG. 24b depicts a perspective view of a connector with a pair of projections defining an opening.

In another embodiment, depicted in FIG. 24b, the locking portion preferably includes two projections 206 and 208 that together define opening 210. The locking portion preferably extends from the connector body to a height from about ¼ the height of the upper portion 202 of the pin 204 to about the height of the upper portion of the pin. Preferably, the height of projections 206 and 208 is approximately equal to the height of the upper portion 202 of the pin.

The pin 204 preferably includes at least one protrusion 211 extending from the upper portion 202 of the pin. The protrusion preferably includes a rounded side 212 and a substantially flat side 214. In FIG. 24b, the protrusion is depicted near the top of the upper portion 202 of the pin 204, however, it should be understood that the protrusion may be located anywhere between the bottom and the top of the upper portion of the pin. The width of the protrusion may vary from about ¼ of the height of the upper portion of the pin to about the height of the upper portion of the pin.

Figure 25A:
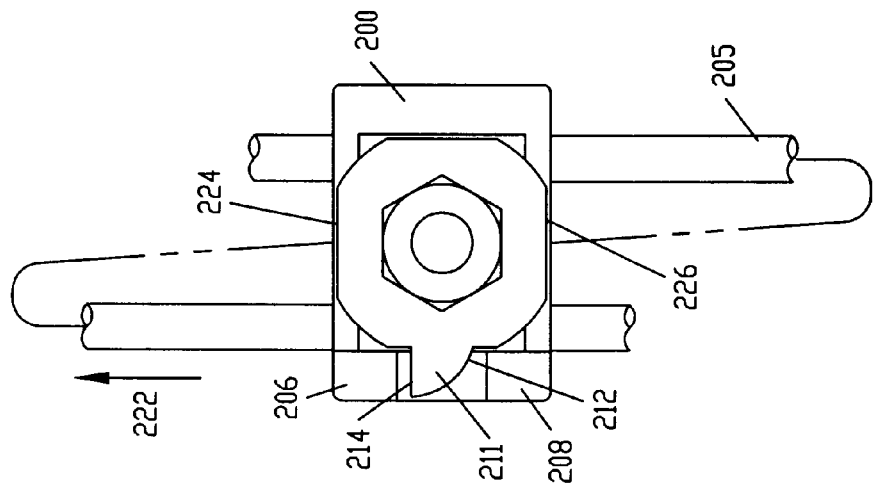
FIG. 25a depicts a top view of a connector with a single locking projection in an unlocked position.
Figure 25B:
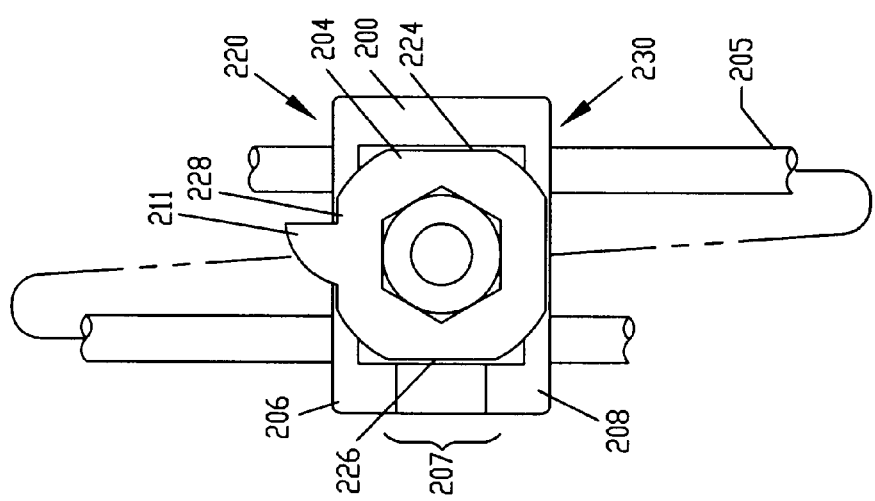
FIG. 25b depicts a top view of a connector with a single locking projection in a locked position.

FIG. 25a depicts a top view of a connector with a pin which includes a protrusion 211 for inhibiting rotation of the pin. The protrusion 211 is preferably oriented away from the locking portion 207 when the pin is in an unlocked position. When the pin is in an unlocked position the cable 205 may be free to move through the connector 200. In FIG. 25b the pin has been rotated in a counter-clockwise direction from the position depicted in FIG. 25a such that the pin is in a locking position. When the pin is in a locking position the cable 205 is preferably inhibited from moving through the connector 200. In the locked position the pin is positioned such that the protrusion 211 now lies within the opening formed by projections 206 and 208. With the protrusion 211 oriented within the opening of the locking portion, rotation of the pin in a clockwise direction may be inhibited. The flat edge 214 of the protrusion 211 preferably engages the flat edge of the projection 206 to inhibit rotation of the pin in a clockwise direction.

While rotation of the pin in a clockwise direction is substantially inhibited, the pin may be turned in a counter-clockwise direction. When rotated in a counterclockwise direction, the rounded edge 212 of the protrusion 211 contacts the projection 208 of the locking portion to slightly inhibit the rotation of the pin. Since the edge 212 of the protrusion contacting the projection 208 is rounded, only a small portion of the rounded edge 212 contacts the projection. By applying sufficient force the rounded edge 212 may cause the projection 208 to deflect slightly outward, providing sufficient space for the protrusion to be rotated past the projection 208 and away from the locking portion. In this manner the pin may be moved into an unlocked position.

During a typical procedure, the cable 205 is preferably formed into a loop and tensioned prior to securing the cable within the connector body 200. After the cable 205 is tensioned the pin is positioned within the internal cavity such that the lower portion of the pin compresses the cable against the wall of the duct, as depicted in FIG. 11. Preferably, the pin is rotated from an unlocked position (shown in FIG. 25a) to a locked position (shown in FIG. 25b) to secure the cable within the connector. When a tensioned cable is secured in this manner, the cable may exert a force in a direction 222 away from the connector, as depicted in FIG. 25b. This force, when exerted on the pin, may rotate the pin in a clockwise direction. If unchecked, the pin may rotate to an unlocked position (i.e., a position in which the cable is no longer secured within the connector). The presence of protrusion 211 upon the pin preferably inhibits this rotation. By inhibiting this rotation the protrusion 211 inhibits loosening of cable 205.

In one embodiment, the pin may have a pair of grooves formed in a lower portion of the pin as has been previously described. The lower portion of the pin preferably fits into the internal cavity. The grooves are preferably positioned such that the cable may be passed through the ducts in the connector when the grooves are aligned with the ducts (see FIG. 10). When the pin is rotated by 90 degrees, the ungrooved portion of the pin preferably engages the cable, thus inhibiting movement of the cable (see FIG. 11). Preferably, the protrusion 211 on the upper portion of the pin is oriented perpendicular to the grooves. Referring to FIGS. 25a and 25b, the grooves of the pin (not shown) are preferably located along sides 224 and 226 of the pin. When the pin is positioned in an unlocked position, as depicted in FIG. 25a, the grooves preferably run parallel to the cable 205 along sides 224 and 226 of the pin. This orientation may allow the cable to move freely through the connector via ducts formed in the connector. A portion of cable 205 may extend into the grooves. The protrusion 211 is preferably positioned on a side perpendicular to sides 224 and 226, such as side 228. In the unlocked position, the pin may be oriented in the connector such that the protrusion 211 extends from the pin in a direction parallel to a portion of the cable, as depicted in FIG. 25a.

When the cable is to be secured within the connector, the pin may be rotated in a counterclockwise direction. This movement causes the sides 224 and 226 of the pin, and therefore the grooves, to preferably move into a perpendicular orientation to the cable 205. The cable preferably comes into contact with the ungrooved portion of the lower section of the pin and is compressed against the ducts inside the connector. This compressive force may secure the cable within the connector. When the pin is positioned in this locking orientation, the protrusion 211 moves into the opening defined by projections 206 and 208. Thus, the action of securing the cable by rotating the pin preferably moves the protrusion into a position such that rotation in a direction opposite to the direction for securing the cable (i.e., a clockwise direction) is inhibited.

Projection 208 of the locking portion is preferably positioned to prevent over turning of the pin. Since a significant amount of force needs to be applied to rotate the pin, it is desired that a stop be present to prevent overturning the pin. Overturning of the pin may lead to realignment of the grooves with the ducts, allowing the cable to become free to move through the connector. The projection 208 of the locking portion preferably prevents this overturning of the pin. The projection 208 provides a stop which the curved edge 212 of the protrusion 211 preferably contacts during rotation of the pin, thus inhibiting further rotation of the pin in a counterclockwise direction. The use of a curved face on the protrusion may allow further counterclockwise rotation if sufficient additional rotational force is applied to the pin.

In another embodiment, a connector including two locking portions may be used in conjunction with a pin including two protrusions, as depicted in FIGS. 26a and 26b. The first locking portion 207 of the connector is preferably oriented opposite a second locking portion 240, as depicted in FIGS. 26a and 26b. The first locking portion preferably includes two projections 206 and 208 which define an opening 209. The second locking portion preferably includes two projections 242 and 244 which define an opening 246. The pin 204 preferably includes two protrusions 211 and 250 oriented opposite to each other. Each protrusion preferably includes a rounded side and a flat side.

The pin preferably has a pair of grooves formed in a lower portion of the pin as has been previously described. The grooves of the pin are preferably located along sides 224 and 226 of the pin. When the pin is positioned in an unlocked position (shown in FIG. 26a), the grooves run parallel to the cable 205 along sides 224 and 226. This orientation may allow the cable 205 to move freely through the connector. In the unlocked position the protrusions are preferably oriented away from locking portions 207 and 240. The protrusions 211 and 250 are preferably positioned on sides perpendicular to sides 224 and 226.

When the cable is to be secured within the connector, the pin may be rotated in a counterclockwise direction. This movement causes the sides 224 and 226 of the pin, and therefore the grooves, to preferably move into a perpendicular orientation to the cable 205. The cable preferably comes into contact with the ungrooved portion of the lower section of the pin and is compressed against the ducts inside the connector. This compressive force may secure the cable within the connector. When the pin is positioned in this locking orientation the protrusions 211 and 250 move into the openings of locking portions 207 and 240. Thus, the action of securing the cable by rotating the pin preferably moves the protrusions into a position such that rotation in a direction opposite to the direction for securing the cable (i.e., a clockwise direction) is inhibited.

The use of two projections and two locking portions has the advantage that the pin may be secured in a locked position whenever the cable is secured within the connector body. Additionally, the two projections may provide increased resistance to rotation of the pin in a clockwise direction when the pin is in a locked position.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims

What is claimed is:

1. A bone fixation system, comprising:
   a body, the body comprising an internal cavity, a duct, and a projection, the duct communicating with the internal cavity, the projection comprising an opening;
   a cable configured to pass through the duct to form a loop for engaging a portion of a bone during use, wherein a portion of the cable extends into the internal cavity during use; and
   a pin comprising a protrusion;
      wherein the pin is positionable within the internal cavity during use in a first position for securing the portion of the cable with respect to the body, and wherein the pin is positionable in a second position during use such that the cable is moveable relative to the body during use;
      and wherein the pin is configured to rotate in a first direction into the first position, and wherein the protrusion is configured to engage the opening when the pin is in the first position, and wherein the engagement of the protrusion with the opening substantially inhibits rotation of the pin in a direction opposite the first direction while allowing further rotation in the first direction during use.

2. The system of claim 1 wherein the duct passes transversally through the body, communicating with the internal cavity, and wherein the duct is in a substantially perpendicular orientation relative to the internal cavity.

3. The system of claim 1 wherein an aperture is positioned between the duct and the internal cavity, wherein the aperture is positioned such that the portion of the cable may extend through the aperture into the internal cavity during use.

4. The system of claim 1 wherein the pin further comprises a groove, the groove having a width substantially greater than a diameter of the cable, the groove being positioned on the pin to allow the cable to freely move past the pin during use.

5. The system of claim 1 wherein the pin further comprises a groove, the groove being adapted to align with the duct during use, and wherein the groove is configured to allow the cable to move through the duct during use.

6. The system of claim 1 wherein the pin further comprises a groove, the groove being oriented substantially perpendicular to the duct when the pin is in the first position during use.

7. The system of claim 1 wherein the pin is configured to compress the cable against the duct such that the cable is secured within the body during use.

8. The system of claim 1 wherein the pin further comprises an upper portion and a lower portion, and wherein the upper portion comprises a diameter substantially greater than a diameter of the lower portion, and wherein the protrusion is formed on the upper portion.

9. The system of claim 1 wherein the pin further comprises an upper portion and a lower portion, and wherein the lower portion comprises a diameter that is substantially less than a diameter of the internal cavity.

10. The system of claim 1 wherein the pin further comprises an upper portion and a lower portion, and wherein the upper portion comprises a diameter that is substantially greater than a diameter of the internal cavity.

11. The system of claim 1 wherein the pin is secured within the internal cavity.

12. The system of claim 1 wherein the pin is configured to rotate from the second position to the first position to secure the portion of the cable with respect to the body during use.

13. The system of claim 1 wherein the pin is configured to rotate from the first position to the second position to permit movement of the portion of the cable through the body during use.

14. The system of claim 1 wherein the pin is configured to rotate in a first direction, and wherein the protrusion is configured to inhibit rotation of the pin in a direction opposite the first direction.

15. The system of claim 1 wherein the pin is configured to rotate in a first direction into the first position, and wherein the protrusion is configured to engage the opening when the pin is in the first position, and wherein the engagement of the protrusion with the opening substantially inhibits rotation of the pin in a direction opposite the first direction.

16. The system of claim 1 wherein the bone is a human spinal vertebra.

17. A bone fixation system, comprising:
   a body comprising an internal cavity, a duct, a first projection and a second projection, the duct communicating with the internal cavity, the first projection and the second projection together defining an opening, wherein the internal cavity passes through the body;
   a cable configured to pass through the duct to form a loop for engaging a portion of a bone during use, wherein a portion of the cable extends into the internal cavity during use; and
   a pin comprising an upper portion, the upper portion comprising a protrusion;
      wherein the pin is positionable within the internal cavity during use in a first position for securing a portion of a cable with respect to the body, and wherein the pin is positionable within the internal cavity during use in a second position such that the cable is moveable relative to the body during use;
      and wherein the protrusion is configured to fit within the opening when the pin is in the first position such that rotation of the pin is substantially hindered during use.

18. The system of claim 17 wherein the duct passes transversally through the body, communicating with the internal cavity, and wherein the duct is in a substantially perpendicular orientation relative to the internal cavity.

19. The system of claim 17 wherein an aperture is positioned between the duct and the internal cavity, wherein the aperture is positioned such that the portion of the cable may extend through the aperture into the internal cavity during use.

20. The system of claim 17 wherein the pin further comprises a groove, the groove having a width substantially greater than a diameter of the cable, the groove being positioned on the pin to allow the cable to freely move past the pin during use.

21. The system of claim 17 wherein the pin further comprises a groove, the groove being configured to align with the duct during use, and wherein the groove is configured to allow the cable to move through the duct during use.

22. The system of claim 17 wherein the pin further comprises a groove, the groove being oriented substantially perpendicular to the duct when the pin is in the first position during use.

23. The system of claim 17 wherein the pin further comprises a lower portion, the lower portion being configured to compress the cable against the duct such that the cable is secured within the body during use.

24. The system of claim 17 wherein the pin further comprises a lower portion, and wherein the upper portion comprises a diameter substantially greater than a diameter of the lower portion.

25. The system of claim 17 wherein the pin further comprises a lower portion, and wherein the lower portion comprises a diameter that is substantially less than a diameter of the internal cavity.

26. The system of claim 17 wherein the upper portion of the pin comprises a diameter that is substantially greater than a diameter of the internal cavity.

27. The system of claim 17 wherein the pin is secured within the internal cavity.

28. The system of claim 17 wherein the first projection and the second projection are positioned a predetermined distance from each other on a side of the body.

29. The system of claim 17 wherein the pin is configured to rotate from the second position to the first position to secure the cable with respect to the body during use.

30. The system of claim 17 wherein the pin is configured to rotate from the first position to the second position to permit movement of a portion of the cable through the body during use.

31. The system of claim 17 wherein the pin is configured to rotate in a first direction, and wherein the protrusion is configured to inhibit rotation of the pin in a direction opposite the first direction.

32. The system of claim 17 wherein the pin is configured to rotate in a first direction into the first position, and wherein the protrusion is configured to engage the opening when the pin is in the first position, and wherein the engagement of the protrusion with the opening substantially inhibits rotation of the pin in a direction opposite the first direction.

33. The system of claim 17 wherein the internal cavity is in a substantially perpendicular orientation to the duct.

34. The system of claim 17 wherein the bone is a human spinal vertebra.

35. A bone fixation system, comprising:
   a body comprising an internal cavity, a duct, a first projection, and a second projection, the first projection comprising a first opening, the second projection comprising a second opening, the duct configured to communicate with the internal cavity, wherein the first projection and the second projection are positioned on opposing sides of the body;
   a cable configured to pass through the duct to form a loop for engaging a portion of a bone during use, wherein a portion of the cable extends into the internal cavity during use; and
   a pin comprising an upper portion, the upper portion comprising a first protrusion and a second protrusion; and wherein the pin is rotatable into a first position for securing the cable with respect to the body, and wherein the pin is rotatable into a second position such that the cable is moveable relative to the body during use;
   and wherein the first protrusion is configured to engage the first opening when the pin is in the first position, and wherein the second protrusion is configured to engage the second opening when the pin is in the first position, and wherein the engagement of the first and second protrusions with the first and second openings substantially hinders rotation of the pin during use.

36. The system of claim 35 wherein the duct passes transversally through the body, communicating with the internal cavity, and wherein the duct is in a substantially perpendicular orientation relative to the internal cavity.

37. The system of claim 35 wherein an aperture is positioned between the duct and the internal cavity, wherein the aperture is positioned such that the portion of the cable may extend through the aperture into the internal cavity during use.

38. The system of claim 35 wherein the pin further comprises a groove, the groove having a width substantially greater than a diameter of the cable, the groove being positioned on the pin to allow the cable to freely move past the pin during use.

39. The system of claim 35 wherein the pin further comprises a groove, the groove being positioned on the pin to align with the duct during use, and wherein the groove allows the cable to move through the body during use.

40. The system of claim 35 wherein the pin further comprises a groove, the groove being oriented substantially perpendicular to the duct when the pin is in the first position during use.

41. The system of claim 35 wherein the pin further comprises a lower portion, the lower portion being configured to compress the cable against the duct such that the cable is secured within the body during use.

42. The connector of claim 35 wherein the pin further comprises a lower portion, and wherein the upper portion comprises a diameter substantially greater than a diameter of the lower portion.

43. The connector of claim 35 wherein the pin is secured within the internal cavity.

44. The connector of claim 35 wherein the pin is configured to rotate from the first position to the second position to permit movement of the cable through the body during use.

45. The connector of claim 35 wherein the pin is configured to rotate from the second position to the first position to secure the cable with respect to the body during use.

46. The connector of claim 35 wherein the pin is configured to rotate in a first direction, and wherein the first and second protrusions are configured to inhibit rotation of the pin in a direction opposite the first direction.

47. The connector of claim 35 wherein the bone is a human spinal vertebra.

48. A bone fixation device, comprising:
   a body comprising an internal cavity, a duct, and a projection, the duct communicating with the internal cavity, the projection comprising an opening, and;
   a pin comprising a protrusion and a groove;
   wherein the pin is configured to fit within the cavity, and wherein the groove and the duct are alignable to receive a cable during use, and wherein the pin is positionable within the cavity during use in a first position such that the groove is substantially aligned with the duct, and wherein the pin is positionable within the cavity in a second position such that the groove is substantially perpendicular to the duct;
   and wherein the pin is configured to rotate in a first direction into the first position, and wherein the protrusion is configured to engage the opening when the pin is in the first position, and wherein the engagement of the protrusion with the opening substantially inhibits rotation of the pin in a direction opposite the first direction while allowing further rotation in the first direction during use.

49. The device of claim 48 wherein the duct passes transversally through the body, communicating with the internal cavity, and wherein the duct is in a substantially perpendicular orientation relative to the internal cavity.

50. The device of claim 48 wherein an aperture is positioned between the duct and the internal cavity.

51. The device of claim 48 wherein the pin further comprises an upper portion and a lower portion, and wherein the upper portion comprises a diameter substantially greater than a diameter of the lower portion, and wherein the protrusion is formed on the upper portion.

52. The device of claim 48 wherein the pin further comprises an upper portion and a lower portion, and wherein the lower portion comprises a diameter that is substantially less than a diameter of the internal cavity.

53. The device of claim 48 wherein the pin further comprises an upper portion and a lower portion, and wherein the upper portion comprises a diameter that is substantially greater than a diameter of the internal cavity.

54. The device of claim 48 wherein the pin is secured within the internal cavity.

55. The device of claim 48 wherein the pin is configured to rotate from the second position to the first position during use.

56. The device of claim 48 wherein the pin is configured to rotate from the first position to the second position during use.

57. The device of claim 48 wherein the pin is configured to rotate in a first direction, and wherein the protrusion is configured to inhibit rotation of the pin in a direction opposite the first direction.

58. The device of claim 48 wherein the pin is configured to rotate in a first direction into the first position, and wherein the protrusion is configured to engage the opening when the pin is in the first position, and wherein the engagement of the protrusion with the opening substantially inhibits rotation of the pin in a direction opposite the first direction.

59. The device of claim 48 wherein the bone is a human spinal vertebra.

60. A method of surgically implanting a surgical cable system comprising:
    passing a cable through a connector, around a human bone element, and back through the connector to form a loop, the connector comprising:
        a body, the body comprising an internal cavity, a duct, and a projection, the duct communicating with the internal cavity, the projection comprising an opening;
        a cable configured to pass through the duct to form a loop for engaging a portion of a bone during use, wherein a portion of the cable extends into the internal cavity during use; and
        a pin comprising a protrusion;
            wherein the pin is positionable within the internal cavity during use in a first position for securing the portion of the cable with respect to the body, and wherein the pin is positionable in a second position during use such that the cable is moveable relative to the body during use;
            and wherein the pin is configured to rotate in a first direction into the first position, and wherein the protrusion is configured to engage the opening when the pin is in the first position, and wherein the engagement of the protrusion with the opening substantially inhibits rotation of the pin in a direction opposite the first direction while allowing further rotation in the first direction during use;
    tensioning the cable using a tensioner; and
    positioning a pin within the connector body, wherein the pin engages the cable to secure the cable within the connector body, thereby fixing a size of the loop.

61. The connector of claim 60, wherein the first protrusion comprises a flat side and a rounded side, wherein the flat side of the protrusion is configured to contact the first locking portion to hinder rotation of the pin in a first direction, and wherein the rounded side of the protrusion is configured to contact the first locking portion when the pin is rotated in a second direction, and wherein the rounded side is configured to substantially hinder rotation of the pin in the second direction.

62. The connector of claim 60, wherein the first protrusion and the second protrusion each comprise a flat side and a rounded side, wherein the flat sides of the protrusions are configured to contact the first locking portion and the second locking portion to hinder rotation of the pin in a first direction, and wherein the rounded sides of the protrusions are configured to contact the first and second locking portions when the pin is rotated in a second direction, and wherein the rounded sides are configured to substantially hinder rotation of the pin in the second direction.

63. The connector of claim 60, wherein the pin is configured to hinder motion of a cable positioned between the pin and the body when the pin is in the first position.

64. The connector of claim 60, wherein the pin is configured to allow motion of a cable positioned between the pin and the body when the pin is in the second position.

65. The conector of claim 60, wherein the first duct and the second duct pass transversally through the body, and wherein the first duct and the second duct are oriented substanially perpendicular to the internal cavity.

66. The connector of claim 60, wherein the pin further comprises a lower section, wherein the lower section has a diameter that is less than a diameter of the inner cavity, and wherein the first and second grooves are located in the lower section.

67. The connector of claim 60, wherein the pin further comprises an upper section, wherein the upper section has a diameter that is greater than a diameter of the inner cavity, and wherein the first and second protrusions are coupled to the upper section.

68. The connector of claim 60, wherein the pin is secured within the internal cavity.

69. The connector of claim 60, wherein the pin is configured to rotate in a first direction, and wherein the first and second protrusions are configured to substantially hinder rotation of the pin in a direction opposite the first direction.

70. The connector of claim 60, wherein the pin is configured to rotate from the second position to the first position during use.

* * * * *